(12) United States Patent
Shelton, IV et al.

(10) Patent No.: US 10,881,403 B2
(45) Date of Patent: Jan. 5, 2021

(54) ENDOCUTTER CONTROL SYSTEM

(71) Applicant: Ethicon LLC, Guaynabo, PR (US)

(72) Inventors: Frederick E. Shelton, IV, Hillsboro, OH (US); Taylor W. Aronhalt, Loveland, OH (US); Jason L. Harris, Lebanon, OH (US); Chester O. Baxter, III, Loveland, OH (US); Mark D. Overmyer, Cincinnati, OH (US); Kris E. Kallenberger, Cincinnati, OH (US); Vincenzo Barbato, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 366 days.

(21) Appl. No.: 15/689,202

(22) Filed: Aug. 29, 2017

(65) Prior Publication Data

US 2019/0059890 A1    Feb. 28, 2019

(51) Int. Cl.
| | |
|---|---|
| *A61B 17/072* | (2006.01) |
| *A61B 17/295* | (2006.01) |
| *A61B 17/00* | (2006.01) |
| *A61B 90/00* | (2016.01) |
| *A61B 17/29* | (2006.01) |

(52) U.S. Cl.
CPC ...... *A61B 17/07207* (2013.01); *A61B 17/295* (2013.01); *A61B 2017/00017* (2013.01); *A61B 2017/00398* (2013.01); *A61B 2017/07285* (2013.01); *A61B 2017/2927* (2013.01); *A61B 2090/066* (2016.02)

(58) Field of Classification Search
CPC .......... A61B 2017/07285; A61B 2017/00017; A61B 2017/2927; A61B 2017/00398; A61B 2090/066; A61B 17/295; A61B 17/07207
See application file for complete search history.

(56) References Cited

U.S. PATENT DOCUMENTS

| | | | |
|---|---|---|---|
| 5,322,055 A | 6/1994 | Davison et al. |
| 5,558,671 A | 9/1996 | Yates |
| 5,579,978 A | 12/1996 | Green et al. |
| 5,792,135 A | 8/1998 | Madhani et al. |

(Continued)

FOREIGN PATENT DOCUMENTS

| | | |
|---|---|---|
| EP | 2777540 A1 | 9/2014 |
| WO | 2014151621 A1 | 9/2014 |

(Continued)

OTHER PUBLICATIONS

U.S. Appl. No. 15/689,198, filed Aug. 29, 2017, Endocutter Control System.

(Continued)

*Primary Examiner* — Thomas M Wittenschlaeger
(74) *Attorney, Agent, or Firm* — Mintz Levin Cohn Ferris Glovsky and Popeo, P.C.

(57) ABSTRACT

Surgical stapling systems and methods for stapling tissue during a surgical procedure are provided. In an exemplary embodiment, a control system is provided for controlling at least one motor coupled to a drive system on a surgical stapling device for driving one or more drive assemblies. The control system can be configured to communicate with the drive system of the stapling tool and to control and modify movement of one or more drive assemblies based on certain feedback.

15 Claims, 12 Drawing Sheets

(56) References Cited

U.S. PATENT DOCUMENTS

| | | |
|---|---|---|
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,120,433 A | 9/2000 | Mizuno et al. |
| 6,132,368 A | 10/2000 | Cooper |
| 6,168,605 B1 | 1/2001 | Measamer et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckal et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 * | 8/2010 | Wales .............. A61B 17/00234 227/175.1 |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,602,286 B2 | 12/2013 | Crainich et al. |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,386,984 B2 * | 7/2016 | Aronhalt .............. A61B 17/068 |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 10,390,841 B2 | 8/2019 | Shelton, IV et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2008/0300580 A1 | 12/2008 | Shelton, IV et al. |
| 2010/0191282 A1 | 7/2010 | Harris et al. |
| 2010/0198248 A1 | 8/2010 | Vakharia |
| 2010/0264193 A1 * | 10/2010 | Huang .................. A61B 17/068 227/176.1 |
| 2011/0015631 A1 | 1/2011 | Wiener et al. |
| 2011/0062211 A1 * | 3/2011 | Ross ................ A61B 17/07207 227/175.1 |
| 2011/0087218 A1 | 4/2011 | Boudreaux et al. |
| 2011/0087256 A1 | 4/2011 | Wiener et al. |
| 2011/0204119 A1 | 8/2011 | McCuen |
| 2011/0290855 A1 | 12/2011 | Moore et al. |
| 2011/0295270 A1 | 12/2011 | Giordano et al. |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0239009 A1 * | 9/2012 | Mollere ........... A61B 17/07207 606/1 |
| 2012/0248167 A1 | 10/2012 | Flanagan et al. |
| 2012/0292367 A1 | 11/2012 | Morgan et al. |
| 2012/0330190 A1 | 12/2012 | Gliner |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005718 A1 | 1/2014 | Shelton, IV et al. |
| 2014/0110453 A1 * | 4/2014 | Wingardner ........... A61B 90/03 227/175.2 |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0263541 A1 | 9/2014 | Leimbach et al. |
| 2014/0263564 A1 * | 9/2014 | Leimbach ............ A61B 17/064 227/180.1 |
| 2014/0276931 A1 | 9/2014 | Parihar et al. |
| 2014/0305993 A1 | 10/2014 | Timm et al. |
| 2015/0173789 A1 * | 6/2015 | Baxter, III ....... A61B 17/07207 606/130 |
| 2015/0196347 A1 | 7/2015 | Yates et al. |
| 2015/0209059 A1 | 7/2015 | Trees et al. |
| 2015/0209573 A1 | 7/2015 | Hibner et al. |
| 2015/0230796 A1 | 8/2015 | Calderoni |
| 2015/0272575 A1 * | 10/2015 | Leimbach ........... A61B 17/072 227/175.3 |
| 2015/0282825 A1 | 10/2015 | Trees et al. |
| 2015/0327851 A1 * | 11/2015 | Kostrzewski ...... A61B 17/3211 227/177.1 |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089533 A1 | 3/2016 | Turner et al. |
| 2016/0174972 A1 * | 6/2016 | Shelton, IV ....... A61B 17/0644 227/180.1 |
| 2016/0174977 A1 * | 6/2016 | Lytle, IV ............. A61B 17/068 227/180.1 |
| 2016/0174978 A1 * | 6/2016 | Overmyer ........ A61B 17/07207 227/178.1 |
| 2016/0175060 A1 | 6/2016 | Park |
| 2016/0287252 A1 | 10/2016 | Parihar |
| 2016/0367243 A1 | 12/2016 | Martin et al. |
| 2017/0000552 A1 | 1/2017 | Asher et al. |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2018/0214168 A1 | 8/2018 | Overmyer et al. |
| 2019/0059889 A1 | 2/2019 | Shelton, IV et al. |
| 2019/0059891 A1 | 2/2019 | Shelton, IV et al. |

FOREIGN PATENT DOCUMENTS

| | | |
|---|---|---|
| WO | 2014151952 A1 | 9/2014 |
| WO | 2017/132611 A1 | 8/2017 |

OTHER PUBLICATIONS

U.S. Appl. No. 15/689,204, filed Aug. 29, 2017, Endocutter Control System.

U.S. Appl. No. 15/200,283 entitled "Methods, Systems, and Devices for Initializing a Surgical Tool" filed Jul. 1, 2016.

U.S. Appl. No. 15/237,653 entitled "Methods, Systems, and Devices for Controlling a Motor of a Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

(56) References Cited

OTHER PUBLICATIONS

U.S. Appl. No. 15/674,075 entitled "Clip Retention for Surgical Clip Applier" filed Aug. 10, 2017.
U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 15/689,072 entitled "Methods, Systems, and Devices for Controlling Electrosurgical Tools" filed Aug. 29, 2017.
U.S. Appl. No. 29/613,511 entitled "Clip Applier Rotation Knob" filed Aug. 10, 2017.

* cited by examiner

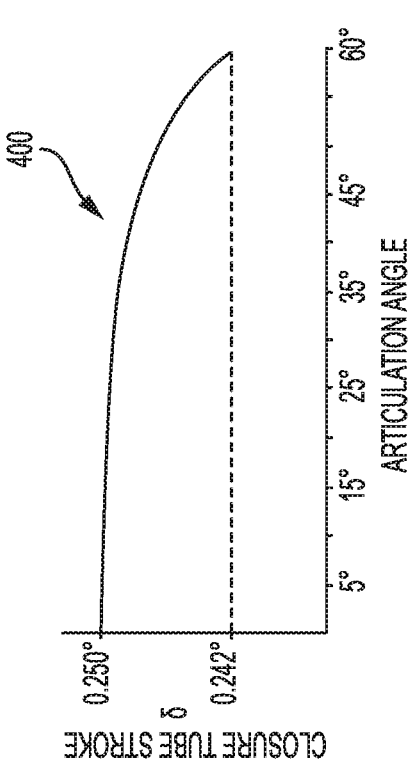
FIG. 7
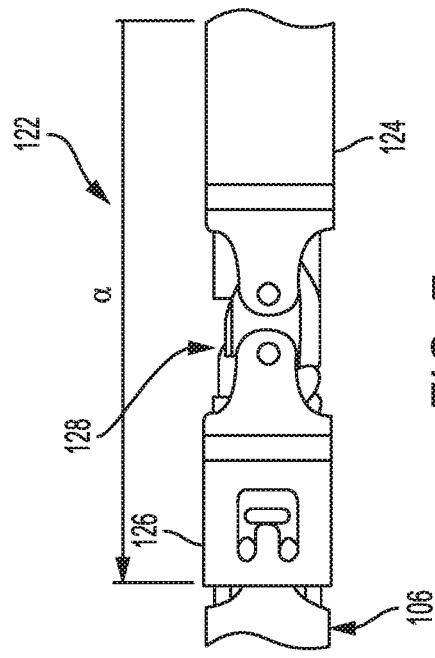
FIG. 8
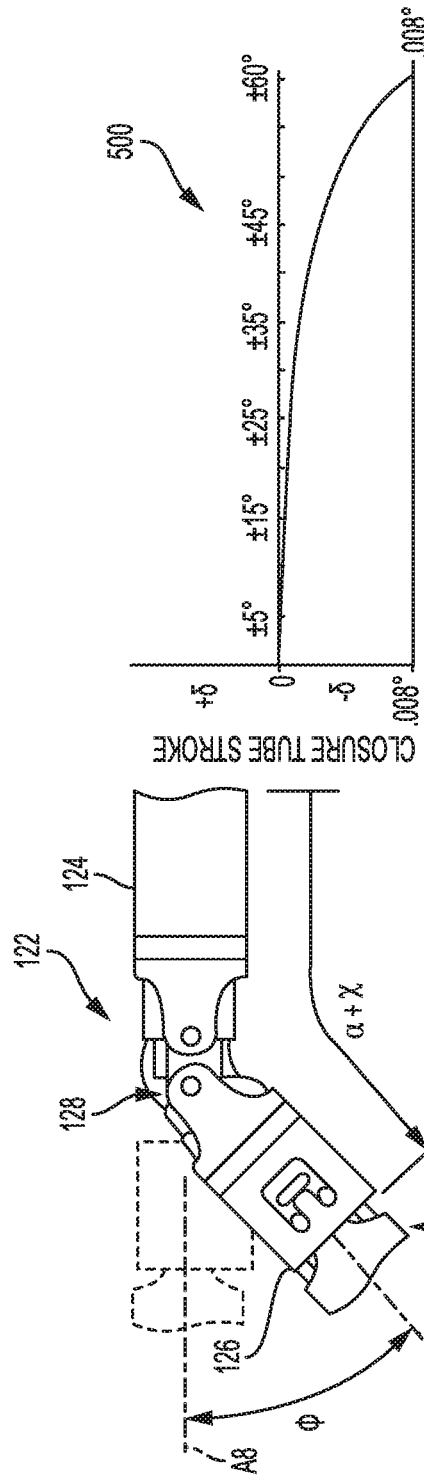
FIG. 9
FIG. 10

ENDOCUTTER CONTROL SYSTEM

FIELD

Electrically-powered surgical staplers and methods for using the same are provided for stapling tissue, such as vessels, other ducts, and the like.

BACKGROUND

More and more surgical procedures are being performed using electrically-powered surgical devices that are either hand-held or coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

Some drawbacks of current surgical staplers are the lack of control and tactile feedback that is inherent in a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a clamping and/or sealing operation (e.g., an actuation button or switch is typically binary and provides no feedback on how much tissue has been cut, etc.) or the forces being encountered (e.g., toughness of the tissue, foreign objects). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices, such as powered surgical staplers, can be unable to accommodate changing loads experienced by the powered surgical stapler. For example, articulation of an end effector position at a distal end of a shaft of the powered surgical stapler can require the powered surgical stapler to increase loads to activate a firing mechanism, such as for cutting and/or stapling tissue. In addition, articulation and increased applied loads can affect the functioning of the powered surgical stapler, including making the powered surgical stapler more prone to malfunctioning and/or damage.

Accordingly, there remains a need for improved devices and methods that address current issues with electrically-powered surgical devices.

SUMMARY

Surgical stapling systems and methods for stapling tissue during a surgical procedures are provided. The surgical stapling system can include a stapling tool having a housing and an elongate shaft assembly extending therefrom with an end effector at a distal end thereof. The end effector can include a first jaw having a staple cartridge with a plurality of staples therein, and a second jaw in the form of an anvil. The first and second jaws can be movable between an open configuration and a closed configuration, and the end effector can be articulatable relative to the elongate shaft assembly. The stapling tool can include a closure assembly configured to move the first and second jaws between the open and closed configurations, an articulation assembly configured to position the end effector at an articulation angle relative to the elongate shaft assembly, and a firing assembly configured to cut tissue engaged between the staple cartridge and the anvil and to progressively drive the plurality of staples through the staple cartridge toward the anvil for stapling tissue engaged between the staple cartridge and the anvil. The surgical stapling system can also include a control system configured to communicate with the stapling tool and to control movement of the firing assembly through a firing stroke to cut tissue and progressively drive the plurality of staples through the staple cartridge toward the anvil. The control system can be configured to modify, based on the articulation angle of the end effector, at least one of a force required to drive the firing assembly and a length of the firing stroke.

The system can vary in a number of ways. For example, the control system can be configured to modify, based on the force required to drive the firing assembly, the length of the firing stroke. In some embodiments, the controls system can be configured to increase the length of the firing stroke as the force required to drive the firing assembly increases. As another example, the control system can be configured to modify, based on the force required to drive the firing assembly, a speed of distal advancement of a firing shaft of the firing assembly. In some embodiments, the control system can be configured to decrease the speed of distal advancement of the firing shaft as the force required to drive the firing assembly increases. As another example, the control system can be configured to increase the force required to drive the firing assembly as the articulation angle increases.

The stapling tool can also have a variety of configurations, and in some embodiments the tool can be a hand-held powered device. In other embodiments, the housing can include a tool mounting portion configured to mount to a motor housing on a surgical robot.

In another embodiment, a surgical stapling system is provided that includes an electromechanical tool. The electromechanical tool can include an elongate shaft having an end effector at a distal end thereof with a first jaw having a staple cartridge with a plurality of staples disposed therein, and a second jaw having an anvil. The first and second jaws can be movable between open and closed positions, and the end effector can be configured to articulate relative to the elongate shaft such that the end effector can be positioned at an articulation angle. The electromechanical tool can also include a housing coupled to the shaft and having one or more drive assemblies. The drive assemblies can include a closure assembly operable to move the first and second jaws between the open and closed positions, an articulation assembly operable to articulate the end effector relative to the elongate shaft, and a firing assembly operable to progressively fire the plurality of staples from the staple cartridge toward the anvil. The surgical stapling system can also include a control system configured to communicate with the electromechanical tool and configured to actuate each of the drive assemblies. In certain embodiments, the control system can be configured to modify operating parameters for one or more of the drive assemblies, such as the firing assembly, based on the articulation angle of the end effector.

The system can vary in a number of ways. For example, the control system can be configured to modify, based on the force required to drive the firing assembly, the length of the firing stroke. In some embodiments, the control system can be configured to increase the length of the firing stroke as the force required to drive the firing assembly increases. As another example, the control system can be configured to modify, based on the force required to drive the firing assembly, a speed of distal advancement of a firing shaft of the firing assembly. In some embodiments, the control system can be configured to decrease the speed of distal advancement of the firing shaft as the force required to drive the firing assembly increases. In some implementations, the control system can be configured to increase the force required to drive the firing assembly as the articulation angle increases.

In another aspect, a method for stapling tissue is provided. The method can include manipulating a surgical stapling device to position tissue between an anvil and a staple cartridge on an end effector of the surgical stapling device, and inputting a command into a control system to cause the control system to initiate actuation of an articulation drive assembly of the surgical stapling device. The articulation drive assembly can cause the end effector to be positioned at an articulation angle relative to an elongate shaft of the surgical stapling device. The method can also include inputting a command into the control system to cause the control system to initiate actuation of a firing drive assembly of the surgical stapling device. The firing drive assembly can move through a firing stroke to move a firing shaft between the anvil and staple cartridge to cut tissue engaged therebetween and progressively drive a plurality of staples through the staple cartridge toward the anvil for stapling tissue engaged therebetween. The control system can modify, based on the articulation angle of the end effector, at least one of a force required to drive the firing drive assembly and a length of the firing stroke.

The method can vary in a number of ways. For example, the control system can modify, based on the force required to drive the firing drive assembly, the length of the firing stroke. As another example, the control system can modify, based on the force required to drive the firing drive assembly, a speed of distal advancement of the firing shaft. As yet another example, the control system can wirelessly communicate with the surgical stapling device to actuate the surgical stapling device. In some implementations, manipulating the surgical stapling device includes manipulating a user input device wirelessly coupled to a surgical robotic system having the surgical stapling device coupled thereto. In other implementations, manipulating a surgical stapling device includes manipulating a handle housing of the surgical stapling device.

In another embodiment, a surgical stapling system is provided that includes a stapling tool having a housing and an elongate shaft assembly extending therefrom with an end effector at a distal end thereof. The end effector can include a first jaw having a staple cartridge with a plurality of staples therein, and a second jaw in the form of an anvil. The first and second jaws can be movable between an open position and a closed position, and the end effector can be articulatable relative to the elongate shaft assembly.

The stapling tool can also include various assemblies. For example, the stapling tool can include a closure assembly having a cam mechanism configured to translate distally to cam the anvil into a fully closed position, an articulation assembly configured to articulate the end effector to a plurality of angular orientations relative to the instrument shaft, and a firing assembly configured to progressively drive the plurality of staples through the staple cartridge toward the anvil for stapling tissue engaged between the staple cartridge and the anvil.

The surgical stapling system can also include a control system that can be configured to communicate with the stapling tool and to control movement of at least one of the articulation assembly, the clamping assembly, and the firing assembly. In certain aspects, the control system can be configured to adjust, during articulation of the end effector, a longitudinal position of the cam mechanism based on an angular orientation of the end effector to thereby maintain the anvil in a fully open position.

The system can vary in a number of ways. For example, the surgical stapling system can be configured such that a change in the longitudinal position of the cam mechanism has a non-linear relationship with the angular orientation of the end effector. As another example, the control system can be configured to cause the cam mechanism to proximally retract as the angular orientation of the end effector increases. As yet another example, the control system can be configured to proximally retract the cam mechanism at an increasing rate as the angular orientation of the end effector increases. In some embodiments, the cam mechanism can include a distal closure tube pivotably coupled to a proximal closure tube. The distal closure tube can be coupled to the anvil such that distal advancement of the cam mechanism causes the distal closure tube to apply a closing force to the anvil thereby moving the anvil from the open position to the closed position.

The surgical stapling tool can be configured as a powered hand-held device, or in other embodiments, the housing can have a tool mounting portion configured to mount to a motor housing on a surgical robot.

In another embodiment, a surgical stapling system is provided that includes an electromechanical tool having an elongate shaft with an end effector at a distal end thereof. The end effector can be configured to articulate relative to the elongate shaft such that the end effector can be positioned in a plurality of angular orientations. The end effector can have a first jaw having a staple cartridge with a plurality of staples disposed therein, and a second jaw having an anvil, with the first and second jaws being movable between open and closed positions.

The electromechanical tool can also include a plurality of drive assemblies including a clamping assembly that can have a cam mechanism configured to translate proximally to cam the anvil into a fully open position, an articulation assembly configured to articulate the end effector to an angular orientation relative to the instrument shaft, and a firing assembly configured to progressively drive the plurality of staples through the staple cartridge toward the anvil for stapling tissue engaged between the staple cartridge and the anvil.

The surgical stapling system can further include a control system configured to communicate with the electromechanical tool and to control one or more of the plurality of drive assemblies. In certain embodiments, the control system can be configured to modify, based on an angular orientation of the end effector and during articulation of the end effector, a longitudinal position of the cam mechanism to thereby maintain the anvil in the fully open position. In other aspects, the control system can be configured to modify, based on an angular orientation of the end effector, a stroke length of the clamping assembly to cause the first and second jaws to move into the closed position.

The surgical stapling system can vary in a number of ways. For example, the surgical stapling system can be configured such that a relationship between a change in the stroke length and a change in the angular orientation of the end effector is non-linear. As another example, the control system can be configured to decrease the stroke length as the angular orientation of the end effector increases. In some implementations, the control system can be configured to decrease the stroke length at an increasing rate as the angular orientation of the end effector increases. In other implementations, a change in the longitudinal position of the closure tube can have a non-linear relationship with the angular orientation of the end effector. As another example the control system can be configured to cause the cam mechanism to proximally retract as the angular orientation of the end effector increases. As yet another example, the control system can be configured to proximally retract the cam mechanism at an increasing rate as the angular orientation of the end effector increases. In some implementations, the cam mechanism can include a distal closure tube pivotably coupled to a proximal closure tube. The distal closure tube can be coupled to the anvil such that distal advancement of the cam mechanism causes the distal closure tube to apply a closing force to the anvil thereby positioning the anvil in the closed position. In other implementations, the housing can include a tool mounting portion configured to mount to a motor housing on a surgical robot.

In another aspect, a method for stapling tissue is provided. The method can include manipulating a surgical stapling device to position tissue between an anvil and a staple deck on an end effector of the surgical stapling device, inputting a command into a control system to cause the control system to initiate actuation of an articulation drive assembly of the surgical stapling device. The articulation drive assembly can move the end effector to position the end effector at an articulation angle relative to an elongate shaft of the stapling device, and the control system can modify a longitudinal position of a clamping assembly of the surgical stapling device based on the articulation angle of the end effector to thereby maintain the anvil in a fully open position.

The method can vary in a number of ways. For example, a relationship between a change in the longitudinal position of the clamping assembly and a change in the articulation angle can be non-linear. As another example, the control system can cause the clamping assembly to proximally retract as the articulation angle increases. As yet another example, the control system can wirelessly communicate with the surgical stapling device to actuate the surgical stapling device. In some implementations, manipulating the surgical stapling device can include manipulating a user input device wirelessly coupled to a surgical robotic system that has the surgical stapling device coupled thereto. In other implementations, manipulating the surgical stapling device can include manipulating a handle housing of the surgical stapling device.

In yet another embodiment, a surgical stapling system is provided and includes an elongate shaft assembly having an end effector at a distal end thereof. The end effector can include a first jaw having a staple cartridge with a plurality of staples therein, and a second jaw in the form of an anvil. The first and second jaws can be movable between an open position and a closed position. The stapling system can also include a firing assembly operably coupled to the end effector and configured to progressively drive the plurality of staples through the staple cartridge toward the anvil for stapling tissue engaged between the staple cartridge and the anvil. A motor can be operably coupled to the firing assembly and it can be configured to actuate the firing assembly. A bailout mechanism can be coupled to the firing assembly and it can be configured to disengage the firing assembly from the motor when the bailout mechanism is activated. The system can also include a control system configured to detect if the bailout mechanism has been actuated by monitoring a load on the motor to determine whether the load is below a predetermined threshold load.

The system can vary in a number of ways. For example, the control system can be configured to monitor the load on the motor during translation of the firing assembly along a travel length. The control system can be configured to detect that the bailout mechanism has been actuated if the monitored load does not exceed the predetermined threshold during translation of the firing assembly along a travel length. Furthermore, the travel length can end before the firing assembly can engage the anvil. Additionally, the travel length can begin a distance after the firing assembly is caused to distally advance toward the anvil. In some implementations the housing can include a tool mounting portion configured to mount to a motor housing on a surgical robot.

In another embodiment, a surgical stapling system is provided that includes a shaft assembly having an end effector with a first jaw having a staple cartridge with a plurality of staples disposed therein, and a second jaw including an anvil. The first and second jaws can be movable between open and closed positions. The surgical stapling system can also include a plurality of drive assemblies operably coupled to the end effector. The plurality of drive assemblies can include a closure assembly configured to move the first and second jaws between open and closed positions, and a firing assembly configured to progressively drive the plurality of staples through the staple cartridge toward the anvil for stapling tissue engaged between the staple cartridge and the anvil. The surgical stapling system can also include a drive housing having at least one motor configured to drive the plurality of drive assemblies, a bailout mechanism coupled to at least one of the plurality of drive assemblies and configured to disengage the at least one drive assembly from the at least one motor when the bailout mechanism is activated, and a control system configured to detect when the bailout mechanism has been actuated by monitoring a load on the at least one motor to relative to a predetermined threshold load.

The system can vary in a number of ways. For example, the control system can be configured to monitor the load on the at least one motor during translation of the firing assembly along a travel length. Furthermore, the control system can be configured to detect that the bailout mechanism has been actuated if the monitored load does not exceed the predetermined threshold during translation of the firing assembly along a travel length.

In some implementations, the at least one motor can be disposed within a housing coupled to a robotic arm on a surgical robot. In other implementations, the at least one motor can be disposed within a handle housing coupled to the shaft assembly.

In another aspect, a method for stapling tissue is provided. The method can include actuating a motor of a surgical stapling device to advance a firing assembly along a travel length toward an anvil of an end effector of the surgical stapling device. A control system can monitor a load on the motor to determine whether a bailout mechanism coupled between the motor and the firing assembly has been actuated and to disengage the motor from the firing assembly if the bailout mechanism is actuated.

The method can vary in a number of ways. For example, the method can include monitoring, by the control system, the load on the motor during activation of the motor to advance the firing assembly along the travel length of the firing assembly. As another example, the travel length can end before the firing assembly can engage the anvil. As yet another example, the method can include determining, by the control system, that the bailout mechanism has been actuated if the load does not exceed a predetermined threshold. In some implementations, the method can include determining, by the control system, that the bailout mechanism has not been actuated if the load exceeds a predetermined threshold.

In another implementation, the control system can wirelessly communicate with the surgical stapling device to actuate the surgical stapling device. In yet another implementation, manipulating the surgical stapling device can include manipulating a user input device that can be wirelessly coupled to a surgical robotic system having the surgical stapling device coupled thereto. As another example, manipulating a surgical stapling device can include manipulating a handle housing of the surgical stapling device.

BRIEF DESCRIPTION OF THE DRAWINGS

This invention will be more fully understood from the following detailed description taken in conjunction with the accompanying drawings, in which:

FIG. 7 is a side view of part of a closure assembly and an articulation assembly of the surgical stapler of FIG. 1;

FIG. 8 is a side view of part of the closure assembly and the articulation assembly shown in FIG. 7, with an end effector of the surgical stapler forming an articulation angle;

FIG. 9 is a stroke length graph showing an example of the control system of FIG. 4 modifying the stroke length of the clamping assembly based on the articulation angle;

FIG. 10 is a closure tube assembly positioning graph showing an example of the control system of FIG. 4 modifying a longitudinal position of the closure tube assembly based on the articulation angle;

DETAILED DESCRIPTION

Figure 1:
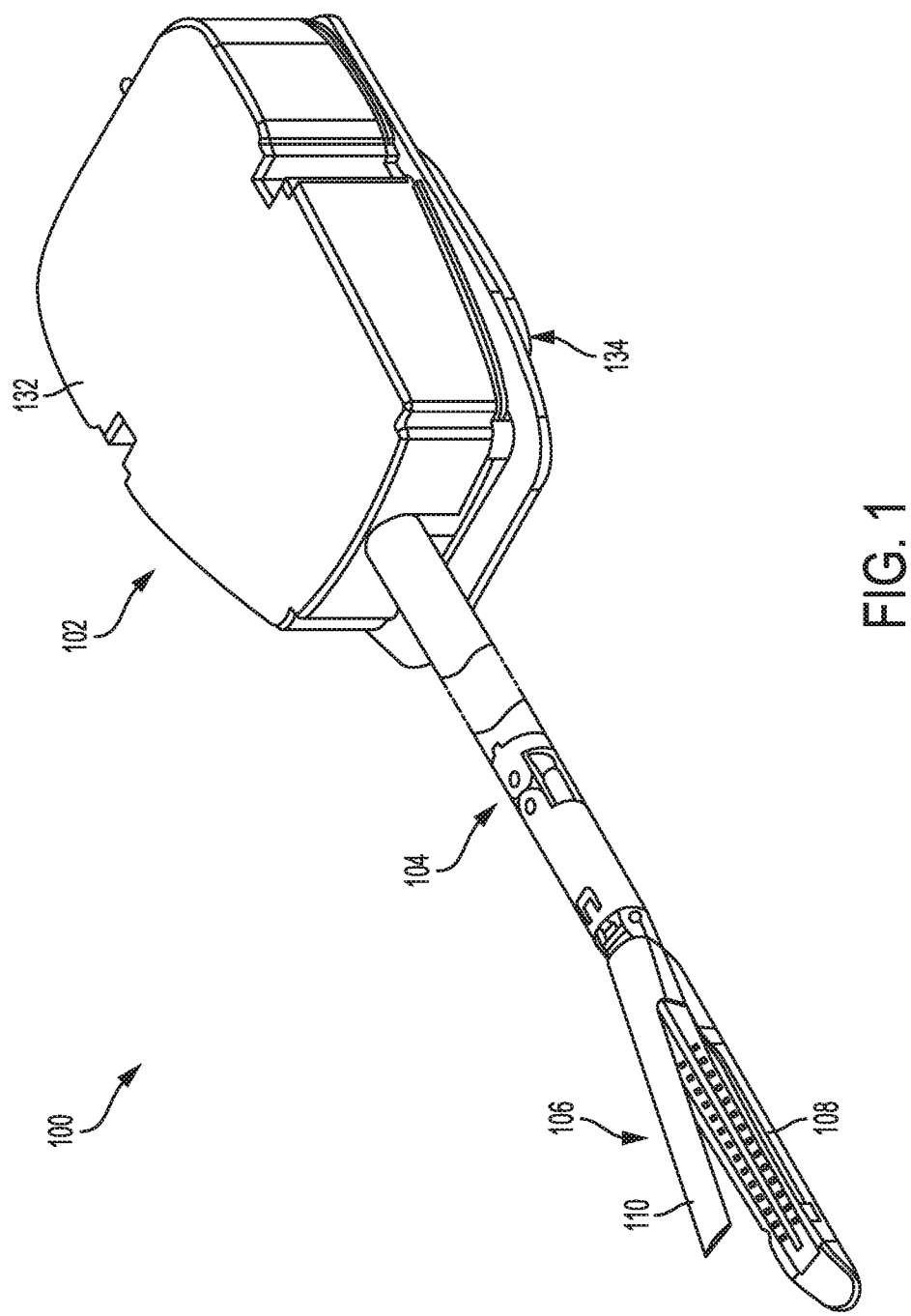
FIG. 1 is a perspective view of one embodiment of a surgical stapler that can be used with a robotic system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Surgical stapling systems and methods for stapling tissue, a vessel, duct, etc., during a surgical procedure are provided. In an exemplary embodiment, a control system is provided for use with an electromechanical surgical stapler or similar device. The surgical stapler can include a housing and an elongate shaft assembly extending therefrom with an end effector at a distal end thereof. The end effector can include a first jaw having a staple cartridge with a plurality of staples therein, and a second jaw in the form of an anvil. The first and second jaws can be movable between an open position and a closed position, and the end effector can articulate relative to the instrument shaft. The elongate shaft assembly can include various actuation assemblies for actuating the device. For example, the device can include a shaft rotation assembly configured to allow the elongate shaft assembly and the end effector to be rotated about a longitudinal axis of the elongate shaft assembly, an articulation assembly configured to allow the end effector to be selectively articulated about a pivot joint, a closure assembly configured to facilitate opening and closing of the jaws, and a firing assembly configured to cut tissue that is clamped between the jaws and to eject staples into the clamped tissue. The device can further include a drive system operably coupled between at least one motor and at least one of the actuation assemblies. In order to control the various actuation assemblies, the control system can be operably coupled to the at least one motor and it can be configured to actuate the at least one motor to drive the drive system(s). The control system can be configured to modify a force being applied to the drive system by the at least one motor based at least in part on one or more predetermined thresholds, such as motor force threshold, and/or a position of one or more actuation assemblies. The control system can allow for powered actuation of the drive system, as opposed to manual actuation via a trigger, and it can enable controlled movement of the actuation assemblies, such as the shaft rotation assembly, the articulation assembly, the closure assembly and/or the firing assembly.

An exemplary surgical stapling system can include a variety of features as described herein and illustrated in the drawings. However, a person skilled in the art will appreciate that the surgical stapling systems can include only some of these features and/or it can include a variety of other features known in the art. The surgical stapling systems described herein are merely intended to represent certain exemplary embodiments. Moreover, while the drive and control systems are described in connection with surgical staplers, these systems can be used in connection with any type of surgical device, such as forceps/graspers, needle drivers, scissors, electrocautery tools, clip appliers/removers, suction tools, irrigation tools, etc. Further, a person skilled in the art will appreciate that the surgical stapling systems described herein have application in conventional minimally-invasive and open surgical instrumentation as well application in robotic-assisted surgery.

Surgical Stapling Device

Figure 2:
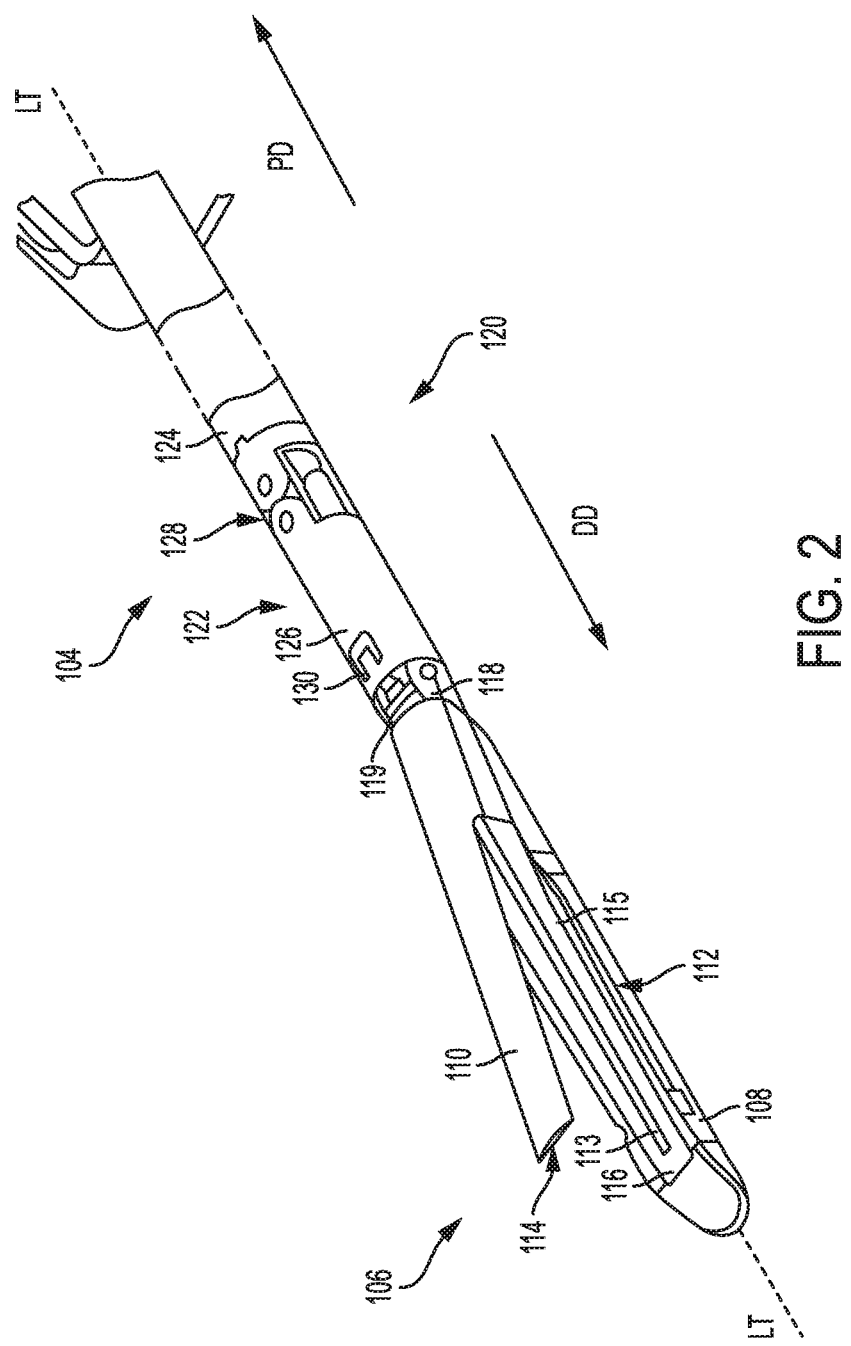
FIG. 2 is an enlarged view of an end effector of the surgical stapler of FIG. 1.
Figure 3:
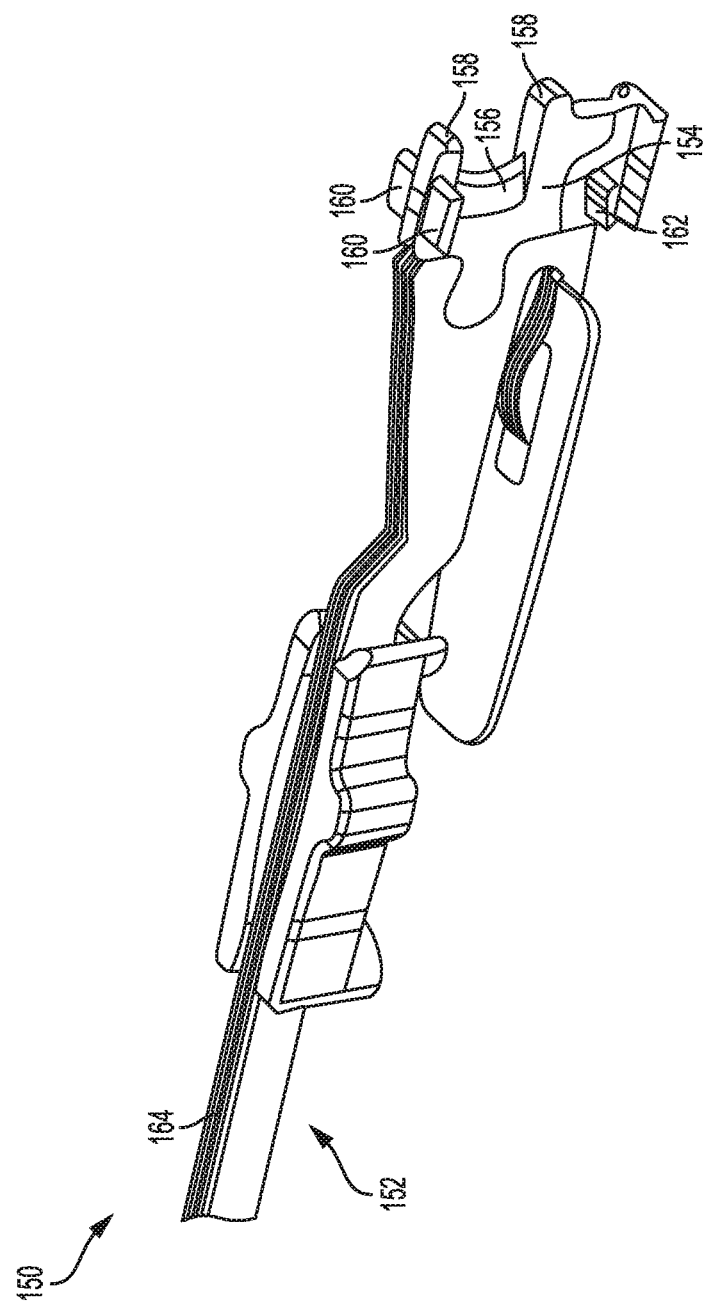
FIG. 3 is a perspective view of a cutting element of the surgical stapler of FIG. 1.

As indicated above, in an exemplary embodiment control systems are provided for controlling actuation of a surgical stapling device. FIGS. 1-3 illustrate one embodiment of a surgical stapler 100 for use with a control system. Additional details on surgical staplers, such as the surgical stapler described herein, are disclosed in U.S. Patent Publication No. 2012/0292367 A1, which is hereby incorporated by reference herein in its entirety.

The illustrated surgical stapler 100 is configured to be used with a robotic system that is operable by inputs from an operator (i.e., a surgeon), however the surgical stapler can be configured as a hand-held device. The illustrated surgical stapler 100 includes a tool mounting portion 102 that is configured to couple to a robotics system. An elongate shaft assembly 104 extends distally from the tool mounting portion 102 along a longitudinal axis LT-LT and an end effector 106 is coupled to a distal end of the of the elongate shaft assembly 104. The elongate shaft assembly 104 can include one or more actuation assemblies. The actuation assemblies can include a closure assembly, an articulation assembly, a shaft rotation assembly, and a firing assembly, which are discussed in more detail below. The end effector 106 has opposed lower and upper jaws 108, 110, although other types of end effectors can be used with the elongate shaft assembly 104, tool mounting portion 102, and components associated with the same.

The tool mounting portion 102 of the surgical stapler 100 can include a drive system 136, which will be discussed in more detail below with respect to FIG. 4. The drive system can be contained within a housing 132 having an interface 134 for mechanically and electrically coupling the tool mounting portion 102 of the surgical stapler 100 to one or more motors of the robotics system.

FIG. 2 shows an enlarged view of the end effector 106 and the elongate shaft assembly 104. As shown in FIG. 2, the lower jaw 108 can include a staple cartridge 112 releasably attached thereto, and the upper jaw 110 can include an anvil 114. The staple cartridge 112 can include a knife channel 113, as well as staple cavities 115 having staples disposed therein. The knife channel 113 can extend longitudinally along the cartridge 112 and can be configured to allow a knife or E-beam to advance therethrough. The anvil 114 can include staple pockets (not shown) that are recessed along an inward tissue-facing surface of the anvil 114. The staple pockets can be arranged along the anvil 114 such that each staple pocket corresponds to a staple cavity 115 of the cartridge 112 for assisting with forming the staples (e.g., stapling tissue together and/or adjunct to tissue). The anvil 114 can also include a knife channel that extends longitudinally along the anvil 114 and is configured to allow a knife or E-beam to advance therethrough.

At least one of the opposed lower and upper jaws 108, 110 can be moveable relative to the other lower and upper jaws 108, 110 to clamp tissue and/or other objects disposed therebetween. The tissue can be clamped between the tissue-facing surface of the anvil, and a tissue-facing surface 116 of the staple cartridge 112. In some implementations, one of the opposed lower and upper jaws 108, 110 may be fixed or otherwise immovable. For example, the upper jaw 110 can be pivotally opened and closed at a pivot point 118 located at a proximal end of the end effector 106, while the lower jaw 108 remains stationary. In some implementations, both of the opposed lower and upper jaws 108, 110 may be movable. The upper jaw 110 can include a tab 119 at its proximal end that can interact with a component of a closure assembly to facilitate opening and closing the upper jaw 110 relative to the lower jaw 108.

Closure Assembly and Closure Drive Assembly

As shown in FIG. 2, the elongate shaft assembly 104 can include a closure tube assembly 122 that is part of a closure assembly configured to move the upper jaw 110 between open and closed positions. The closure tube assembly 122 can include a proximal closure tube 124 and a distal closure tube 126 that are pivotably linked therebetween at a pivot joint 128. The distal closure tube 126 can include an opening 130 into which the tab 119 of the upper jaw 110 can be inserted in order to facilitate opening the jaws 108, 110 of the end effector 106 as the distal closure tube 126 is retracted longitudinally in a proximal direction PD. The jaws 108, 110 can be closed by moving the distal closure tube 126 in a distal direction DD.

Figure 4:
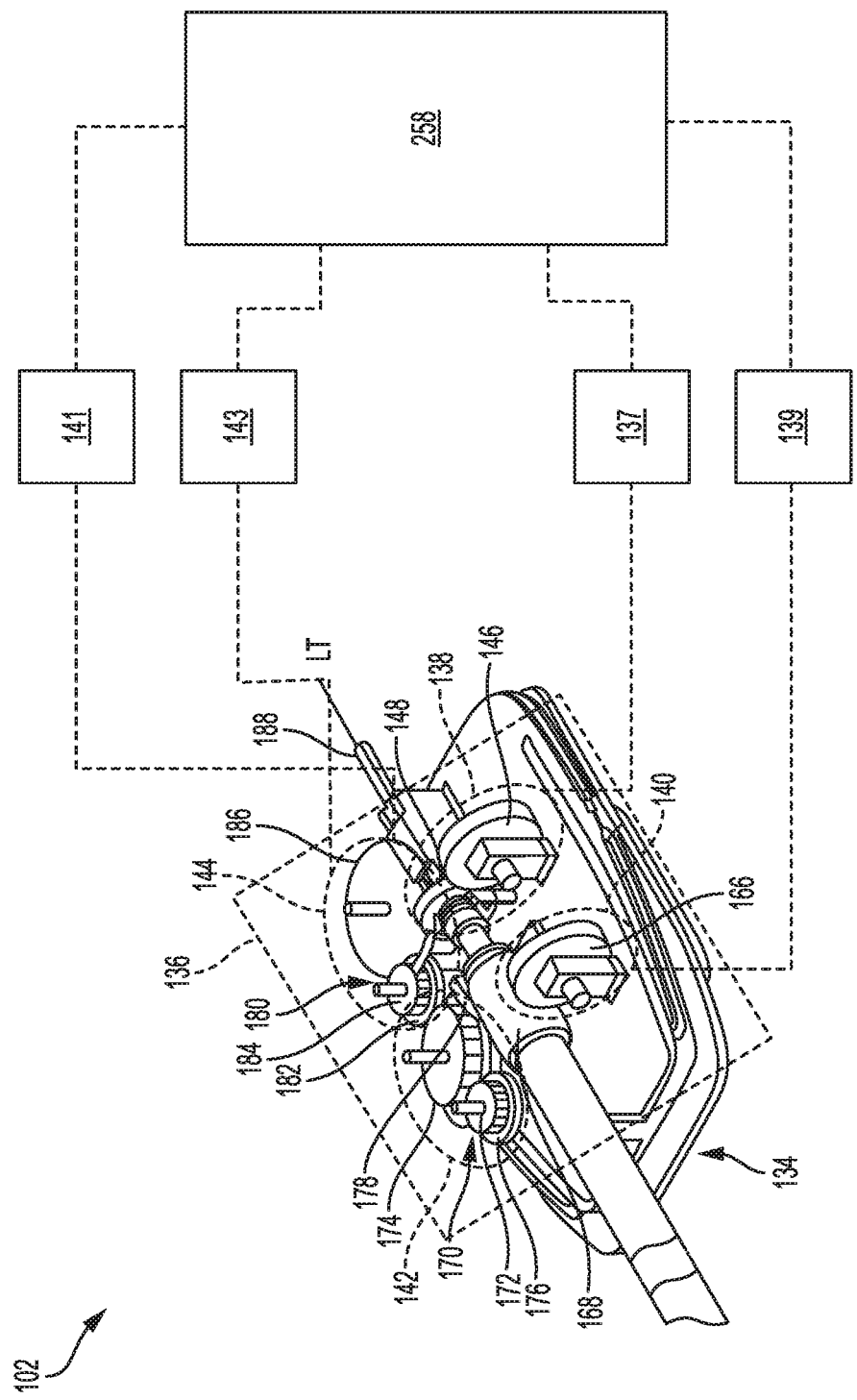
FIG. 4 is a perspective, partially schematic view of the surgical stapler of FIG. 1 with a portion of the housing removed and showing motors of the surgical stapler coupled to a control system.

The closure tube assembly 122 can be operably coupled to a closure drive assembly 142 of the drive system 136 shown in FIG. 4. The closure drive assembly 142 can translate force from a motor to the closure tube assembly 122 to move the upper jaw 110 between open and closed positions. While the closure drive assembly 142 can have a variety of configurations, in some embodiments, as shown in FIG. 4, the closure drive assembly 142 can include a closure reduction gear set 170. The closure reduction gear set 170 can include a first closure drive gear 172 that is in meshing engagement with a second closure drive gear 174. The second closure drive gear 174 is in meshing engagement with a closure rack gear of a closure sled 178 that is coupled to the closure tube assembly 122 at a position proximal of the tube gear segment 168. The closure reduction gear set 170 can also include a driven gear 176 that is in meshing engagement with a closure spur gear. The closure spur gear is configured to be operably coupled to one or more motors of the robotic system, as will be discussed in greater detail below.

When the closure drive assembly 142 is actuated, the closure spur gear drives the driven gear 176 and the first closure drive gear 172. Rotation of the first closure drive gear 172 drives the second closure drive gear 174, thereby driving the closure sled 178 axially. Axial motion of the closure sled 178 drives the closure tube assembly 122 axially. The axial direction in which the closure tube assembly 122 moves ultimately depends on the direction in which the closure spur gear is rotated. For example, if the spur gear is rotated in a first direction, the closure sled 178, and therefore the closure tube assembly 122, will be driven in the distal direction. As the distal closure tube 126 is driven distally, the end of the distal closure tube 126 will engage a portion of the upper jaw 110 and cause the upper jaw 110 to pivot to a closed position. If the spur gear is rotated in a second direction, opposite the first direction, the closure sled 178 and the closure tube assembly 122 will move in a proximal direction. As the distal closure tube 126 is drive in the proximal direction, the opening 130 of the distal closure tube 126 interacts with the tab 119 of the upper jaw 110, thereby pivoting the upper jaw 110 to an open position.

Articulation Assembly and Articulation Drive Assembly

The elongate shaft assembly 104 of the surgical stapler 100 can also include an articulation assembly. The articulation assembly is configured to selectively articulate (i.e., angularly orient) the end effector 106 about an articulation joint 120 located along the length of the elongate shaft assembly 104.

The articulation assembly can be operably coupled to an articulation drive assembly 138 of the drive system 136. The articulation drive assembly 138 can translate force from a motor to articulate the end effector 106 about the articulation joint. While the articulation drive assembly 138 can have a variety of configurations, in some embodiments, as shown in FIG. 4, the articulation drive assembly 138 can include an articulation drive gear 146 in meshing engagement with an articulation nut 148. The articulation drive gear 146 is mechanically coupled to a portion of the shaft assembly 104. The articulation drive assembly 138 can also include a spur gear that is in meshing engagement with the articulation drive gear 146. When the articulation drive assembly 138 is activated, the spur gear drives the articulation drive gear 146, thereby causing rotation of the articulation nut 148 which causes articulation of the end effector 106 about the articulation joint 120.

Shaft Rotation Assembly and Rotational Drive Assembly

The elongate shaft assembly 104 of the surgical stapler 100 can also include a shaft rotation assembly. The shaft rotation assembly is configured to rotate the elongate shaft assembly 104 and the end effector 106 about the longitudinal axis LT.

The shaft rotation assembly can be operably coupled to a rotational drive assembly 140 of the drive system 136. The rotational drive assembly 140 can translate force from a motor to rotate the elongate shaft assembly 104 and end effector 106. While the rotational drive assembly 140 can have a variety of configurations, in some embodiments, as shown in FIG. 4, the rotational drive assembly 140 can include a rotary driven gear 166 that is in meshing engagement with a tube gear segment 168 formed on (or attached to) the proximal end of the proximal closure tube 124. The rotational drive assembly 140 can also include a rotation drive gear that is in meshing engagement with a rotary driven gear 166. When the rotational drive assembly 140 is activated, the rotation drive gear drives the rotary driven gear 166, thereby causing rotation of the shaft assembly 104 and the end effector 106.

Firing Assembly and Firing Drive Assembly

The elongate shaft assembly 104 of the surgical stapler 100 can also include a firing assembly that is configured to eject staples into tissue clamped between the jaws 108, 110 and to cut the clamped tissue. FIG. 3 shows an example of a firing shaft 150 that can be part of the firing assembly of the surgical stapler 100. The firing shaft 150 can include a flexible bar 152 having an E-beam 154 coupled to a distal end thereof. The E-beam 154 can have a knife blade 156, or other cutting element, coupled to a distal surface thereof. The knife blade 156 is configured to cut tissue as staples are ejected. As illustrated, the E-beam 154 can include guides 158 that extend distally, as well as upper and lower lateral guides 160, 162 that extend laterally. At least one of the guides 158 can be configured to engage a wedge sled within the staple cartridge 112, which in turn can push staple drivers upwardly through the staple cavities 115 formed in the staple cartridge 112 to fire staples. During firing, lateral guides 160, 162 are positioned within portions of the upper and lower jaws 110, 108, and can extend laterally outward beyond the knife channel of the anvil 114 and the knife channel 113 of the cartridge to prevent the jaws 110, 108 from opening during firing.

As described above, the end effector 106 can be articulated about the articulation joint 120. Accordingly, the flexible bar 152 can be designed to be flexible such that it can bend laterally to accommodate articulation, while being rigid enough to push the knife blade 156 through the end effector 106 when an axial load is applied during firing. In some embodiments, the flexible bar 152 is made of a number of ligation bands 164 that are slidable relative to each other thereby allowing the ligation bands 164 to splay as the flexible bar is caused to bend during articulation of the end effector. Splaying occurs as a result of each ligation band bending at a different radius of curvature when the end effector 106 is articulated. For example, if the end effector 106 is articulated to the left, a distal end of a left-most ligation band will extend farther along the length of the elongate shaft assembly 104 than a distal end of a right-most ligation band.

The knife blade 156 can be positioned adjacent to, or within, the end effector 106, and the flexible bar 152 can extend within the closure tube assembly 122, for example, within a longitudinal firing bar slot of the elongate shaft assembly 104. The flexible bar 152 can extend proximally from the end effector 106, toward the tool mounting portion 102, to a position that is proximal of the articulation joint 120. A proximal end of the flexible bar 152 can be coupled to a distal end of a firing bar, and a proximal end of the firing bar can be coupled to one or more components within the tool mounting portion 102. Accordingly, the firing shaft 150 can be configured to be driven distally by the firing bar thereby causing cutting of tissue between the jaws and firing of staples contained within the staple cartridge 112.

The firing assembly can be operably coupled to a firing drive assembly 144 of the drive system 136. The firing drive assembly 144 can translate force from a motor to the firing assembly to translate the firing shaft 150. While the firing drive assembly 144 can have a variety of configurations, in some embodiments, as shown in FIG. 4, the firing drive assembly 144 can include a knife drive reduction set 180 that includes a first knife drive gear 182 and a second knife drive gear 184. The second knife drive gear 184 is in meshing engagement with a third knife drive gear 186 and meshing engagement with a knife rack gear 188. The knife rack gear 188 can be rotatably coupled to a distal end of the firing bar that is coupled to the flexible bar 152 of the firing shaft 150. Such a configuration can allow the firing bar to rotate freely, relative to the knife rack gear 188. The firing drive assembly 144 can also include a knife spur gear (obscured) that is in a meshing engagement with the first knife drive gear 182, the knife spur gear being operably couple to the firing motor 143 via the interface 134. When activated, the knife spur gear can drive the first knife drive gear 182 and the second knife drive gear 184. The second knife drive gear 184 can drive the third knife drive gear 186, which drives the knife rack gear 188 axially. Accordingly, since the firing shaft 150 is mechanically coupled to the knife rack gear 188, it will be driven axially with the knife rack gear 188. It will be appreciated that the application of a rotary output motion from the firing motor 143 in one direction will result in the axial movement of the firing shaft 150 of the firing assembly in a distal direction and application of the rotary output motion in an opposite direction will result in the axial travel of the firing shaft 150 in a proximal direction.

As indicated above, various embodiments of drive and control systems are provided for producing real-time feedback during operation of electrically-powered surgical stapling devices thereby allowing a surgeon or other user to effectively and accurately use such device. In general, the drive system is operably coupled between at least one motor and at least one drive assembly, such as the shaft rotation assembly, the articulation assembly, the jaw closure assembly, and/or the firing assembly. The control system is operably coupled to the at least one motor and is configured to actuate the at least motor to drive the drive system and thereby control movement and operations of the various drive assemblies, i.e., the shaft rotation assembly, the articulation assembly, the jaw closure assembly, and/or the firing assembly. We discuss the motors, the drive system, the drive assemblies, and the control system in more detail below.

Motors

As indicated above, one or more motors can be used to drive the various drive assemblies of the surgical device. As discussed above, each drive assembly can include various components, such as one or more gears that receive a rotational force from the motor(s) and that transfer the rotational force to one or more drive shafts to cause rotary or linear motion of the drive shaft(s). The motor(s) can be located within the surgical device itself or, in the alternative, coupled to the surgical device such as via a robotic surgical system. Each motor can include a rotary motor shaft that is configured to couple to the one or more drive assemblies of the surgical device so that the motor can actuate the one or more drive assemblies to cause a variety of movements and actions of the device.

Exemplary motors for use with the systems disclosed herein are described, for example, in U.S. Pat. Nos. 9,445, 816 and 9,585,658 and in U.S. Patent Publication Nos. 2012/0292367, 2013/0325034, and 2015/0209059.

It should be noted that any number of motors can be used for driving any one or more drive assemblies on a surgical device. For example, one motor can be used to actuate two different drive assemblies for causing different motions. In certain embodiments, the drive system can include a shift assembly for shifting the drive system between different modes for causing different actions. A single motor can in other aspects be coupled to a single drive assembly. A surgical device can include any number of drive assemblies and any number of motors for actuating the various drive assemblies. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to determine and/or monitor at least one of displacement of a drive assembly coupled to the motor or a force on the motor during actuation of the drive assembly. For example, a rotary encoder can be coupled to the motor to monitor the rotational position of the motor, thereby monitoring a rotational or linear movement of a respective drive assembly coupled to the motor. Alternatively or in addition, a torque sensor can be coupled to the motor to determine or monitor an amount of force being applied to the motor during device operation. It is also contemplated that other ways to determine or monitor force on the motor can include (i) measuring current though the motor by using a sensor or a meter device; or (ii) measuring differences between actual velocity of the motor or components, which may include a combination of a distance travelled and an expired time, and the commanded velocity.

In certain embodiments, when the at least one motor is activated, its corresponding rotary motor shaft drives the rotation of at least one corresponding gear assembly in the drive system. The drive or gear assembly is coupled to at least one corresponding drive shaft of a drive assembly, thereby causing linear and/or rotational movement of the drive shaft. While movement of two or more drive shafts can overlap during different stages of operation of the drive system, each motor can be activated independently from each other such that movement of each corresponding drive shaft does not necessarily occur at the same time or during the same stage of operation.

FIG. 4 illustrates an exemplary embodiment of a drive system 136 contained within the housing 132 of the tool mounting portion 102. The drive system 136 is shown operatively coupled to a plurality of motors, such as a closure motor 141 configured to drive the closure drive assembly 142 thereby actuating the closure assembly, an articulation motor 137 configured to drive the articulation drive assembly 138 thereby articulating the end effector 106, a rotation motor 139 configured to drive the rotational drive assembly 140 thereby rotating the shaft assembly 104 and end effector 106, and a firing motor 143 configured to drive the firing drive assembly 144 thereby driving the firing drive assembly 144. The motors 137, 139, 141, 143 can be operably coupled to a control system 258 that can control activation of the motors 137, 139, 141, 143. The control system 258 is discussed in more detail below. A person skilled in the art will appreciate that the motors and control system can be located within the tool housing 132 to form a powered hand-held device, or they can be located external of the housing 132, such as in a robotic system as described with respect to FIG. 5. Exemplary hand-held devices that can include the motors and control system disclosed herein are disclosed, for example, in U.S. Patent Publication No. 2013/0261648 and U.S. Patent Publication No. 2015/0272575, each of which is incorporated by reference herein in its entirety.

As indicated above, the motors as well as the control system can be disposed within the handle housing, like housing 132 shown in FIG. 1, or can be located outside of the handle housing, such as within a surgical robotic system. Over the years a variety of minimally invasive robotic (or "telesurgical") systems have been developed to increase surgical dexterity as well as to permit a surgeon to operate on a patient in an intuitive manner. Many of such systems are disclosed in the following U.S. Patents, which are each herein incorporated by reference in their respective entirety: U.S. Pat. No. 5,792,135 entitled "Articulated Surgical Instrument For Performing Minimally Invasive Surgery With Enhanced Dexterity and Sensitivity," U.S. Pat. No. 6,132,368 entitled "Multi-Component Telepresence System and Method," U.S. Pat. No. 6,231,565 entitled "Robotic Arm DLUS For Performing Surgical Tasks," U.S. Pat. No. 6,783,524 entitled "Robotic Surgical Tool With Ultrasound Cauterizing and Cutting Instrument," U.S. Pat. No. 6,364,888 entitled "Alignment of Master and Slave In a Minimally Invasive Surgical Apparatus," U.S. Pat. No. 7,524,320 entitled "Mechanical Actuator Interface System For Robotic Surgical Tools," U.S. Pat. No. 7,691,098 entitled "Platform Link Wrist Mechanism," U.S. Pat. No. 7,806,891 entitled "Repositioning and Reorientation of Master/Slave Relationship in Minimally Invasive Telesurgery," and U.S. Pat. No. 7,824,401 entitled "Surgical Tool With Wristed Monopolar Electrosurgical End Effectors." Many of such systems, however, have in the past been unable to generate the magnitude of forces required to effectively cut and fasten tissue.

Control System

Figure 5:
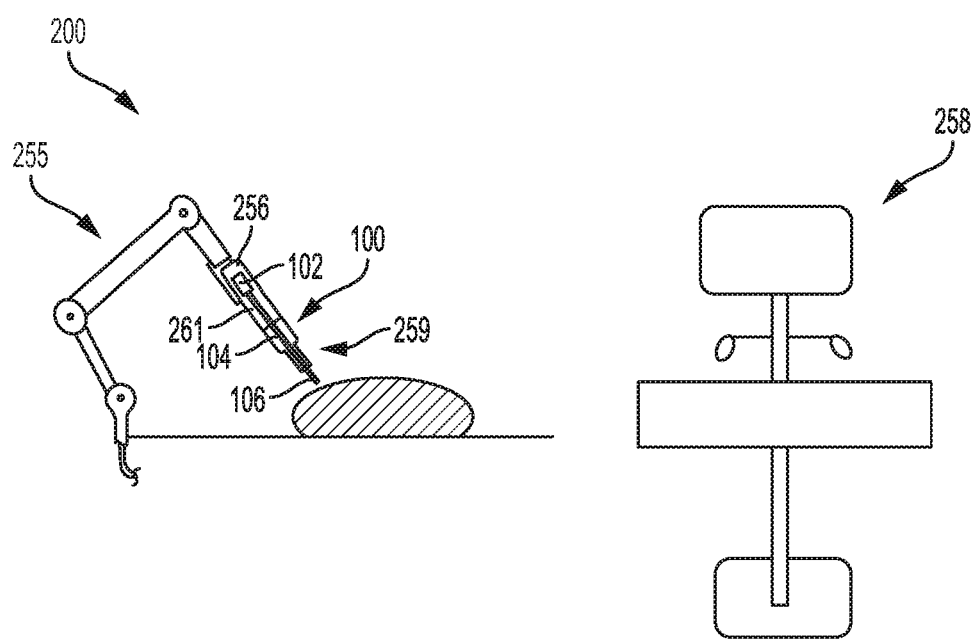
FIG. 5 is a perspective view of an exemplary embodiment of a surgical robotic system that includes a robotic arm having the surgical stapler of FIG. 1 mounted thereon, and being wirelessly coupled to a control system.

FIG. 5 illustrates an exemplary embodiment of surgical robotic system 200 that includes a robotic arm 255 that is wirelessly coupled to a control system 258 having a console with a display and two user input devices. One or more motors, such as the motors 137, 139, 141, 143 shown in FIG. 4, are disposed within a motor housing 256 that is coupled to an end of the robotic arm 255. The tool mounting portion 102 is configured to be seated within the motor housing 256 and the interface 134 on the tool mounting portion 102 functions to mechanically and electrically couple the drive system 136 in the tool mounting portion 102 to the motors within the motor housing 256. As a result, when the motor(s) are activated by the control system 258, the motor(s) can actuate the drive system 136 in the surgical stapler 100. As shown in FIG. 5, the elongate shaft assembly 104 extends from the tool mounting portion 102. During surgery, the elongate shaft assembly 104 can be placed within and extend through a trocar 259 that is mounted on the bottom of a carrier 261 extending between the motor housing 256 and a trocar support. The carrier 261 allows the surgical stapler 100 to be translated into and out of the trocar 259.

As discussed above, the control system 258 and motor(s) can power and control various drive assemblies of the surgical stapler 100, such as the firing assembly, the closure assembly, the shaft rotation assembly, and the articulation assembly. Unlike manually-operated devices, electrically-powered surgical devices can lack control and tactile feedback, thereby reducing a surgeon's ability to effectively, accurately, and safely use these devices. Further, manually-operated devices are typically displacement controlled in which mechanical hard stops are used to control displacement of the various drive assemblies. However, using mechanical stops in an electrically-powered device has its disadvantages. For example, a user can be limited in assessing whether a jam has occurred in the device Of if the staple has been prematurely dislodged from the device during use.

Referring to FIG. 4, as discussed above, the motors 137, 139, 141, 143 can be operably coupled to respective gear assemblies in the drive system, which in turn are coupled to drive assemblies 138, 140, 142, 144. In order to drive the drive assemblies, the motors 137, 139, 141, 143 can be operably coupled to the control system 258 such that the control system 258 can control the motors 137, 139, 141, 143. As described above, one or more motors can be coupled to a rotary encoder that provides linear and/or rotary displacement information to the control system 258. Such displacement information can be used by the control system 258 to appropriately control one or more of the drive assemblies to thereby control associated actuation assemblies. Alternatively or in addition, the one or more motors can be coupled to a corresponding torque sensor that provides the control system 258 with information about the amount of force being applied to the motor(s) during operation of the drive system 136, which can also be used by the control system 258 to appropriately control one or more of the drive assemblies to thereby control associated actuation assemblies.

The control system 258 can communicate with the motors using various techniques, such as via a direct wired connection or using wireless communication. Various wireless communication embodiments are described in U.S. patent application Ser. No. 13/118,259 to James R. Giordano et al. filed on May 27, 2011, the disclosure of which is herein incorporated by reference in its entirety.

Operation of Control System

Generally, the control system can control movement and actuation of a surgical device. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s) that sense speed, displacement, and/or torque of the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

A person skilled in the art will appreciate that, while control systems are shown and described below with respect to drive systems configured for tissue stapling and cutting devices, the control systems disclosed herein can be coupled to drive systems that are configured for other surgical staplers or devices, such as forceps/graspers, needle drivers, scissors, electrocautery tools, clip appliers/removers, suction tools, irrigation tools, etc.

Detection of Bailout Activation

Surgical staplers can include a bailout actuator that, when actuated by a user or control system, actuates a bailout mechanism that places the surgical stapler in a bailout mode thereby preventing further advancement of the firing shaft (e.g., the firing shaft 150 in FIG. 3) and opening the jaws. Such activation of the bailout actuator can be in response to a detected error related to the surgical system, such as damage to the surgical stapler, an object stuck between the jaws thereby preventing the firing shaft 150 from advancing, etc. Upon activation of the bailout actuator, the bailout mechanism causes at least the firing shaft 150 and closure tube assembly 122 to proximally retract thereby allowing the jaws to open. Once retracted, the bailout mechanism permanently decouples a motor (e.g., firing motor 143 in FIG. 4) from the firing drive assembly 144. As such, activation of the bailout mechanism ensures that the surgical stapler is unable to subsequently activate the firing assembly. Since activation of the bailout mechanism permanently disables the firing assembly, surgical errors can be made and procedure times prolonged if the disabled surgical stapler is attempted to be reused.

A surgical stapler can include a sensor or switch that detects whether a door covering a bailout actuator has been manipulated (e.g., opened) thereby indicating that the bailout mechanism has been activated. Such detection of the door covering the bailout actuator can be unreliable and does not directly test whether the bailout mechanism was actually activated. Accordingly, the control system 258 can be configured to run a bailout test cycle that can provide a reliable way for the control system 258 to determine whether or not the bailout mechanism has been activated.

In an exemplary embodiment, when the control system 258 receives a signal from the sensor that a door covering a bailout actuator has been opened, the control system can begin the bailout test cycle. This test cycle can include activating the firing motor 143 to attempt to distally advance the firing shaft 150. The control system 258 can monitor the torque applied by the firing motor 143 to determine whether the firing motor 143 is disengaged from the knife drive assembly 144. For example, the bailout test cycle can include a predefined bailout threshold that defines a threshold level of torque the firing motor 143 must exceed while attempting to advance the firing shaft 150 along a predefined travel distance in order for the control system 258 to determine that the surgical stapler 100 has not been placed in bailout mode. The control system 258 can automatically run the bailout test cycle after the surgical stapler 100 has been coupled to the robotic system, such as when power is provided to the surgical device 100, or any time prior to firing of the firing assembly. Further details of the bailout test cycle, including parameters analyzed by the control system 258, are described in greater detail below.

Figure 6:
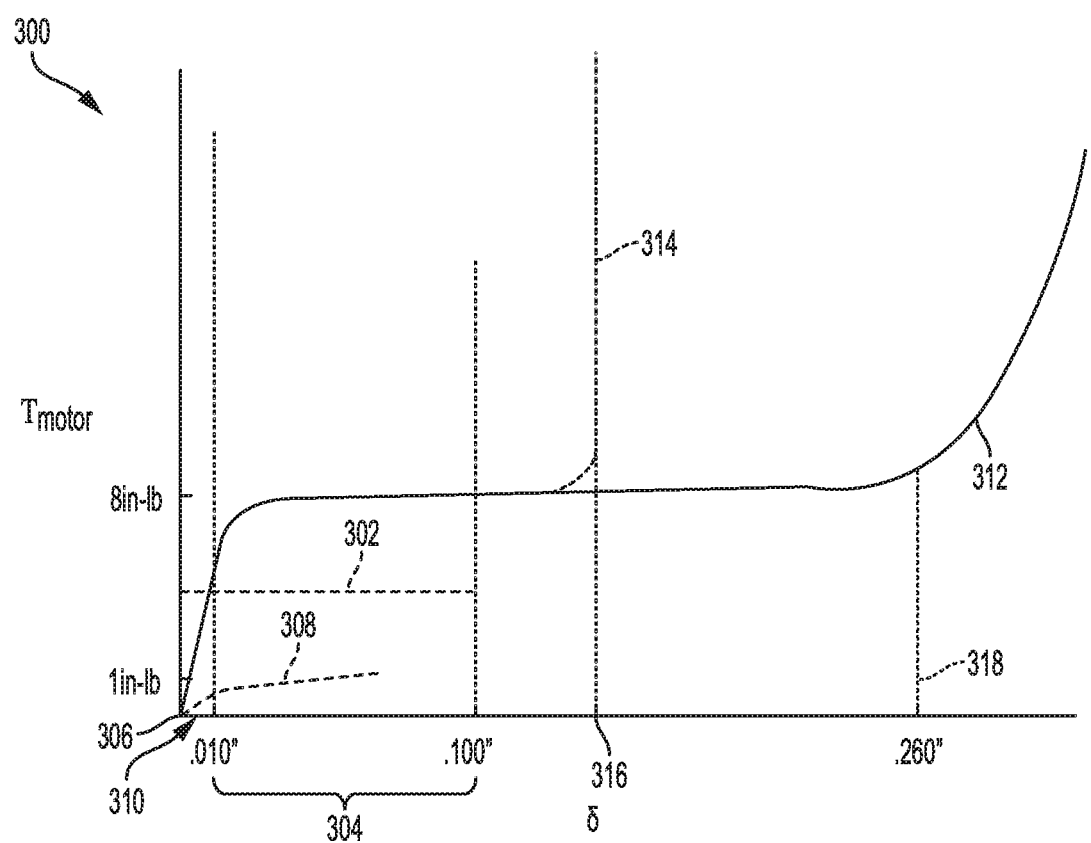
FIG. 6 is a bailout detection graph showing a number of parameters analyzed by a control system during performance of a bailout test cycle.

FIG. 6 illustrates a bailout detection graph 300 including a number of parameters analyzed by the control system 258 during performance of the bailout test cycle. FIG. 6 illustrates the measured torque of the firing motor 143 as a function of a distance traveled by the firing shaft 150 in the distal direction. As discussed above, such distance traveled by the firing shaft 150 is determined by one or more sensors and/or encoders associated with the firing motor 143 that determine an expected distance traveled by the firing shaft 150 based on a number of rotations of the firing motor 143.

The bailout detection graph 300 illustrates a predefined bailout detection threshold 302 and a detection zone 304. The detection zone 304 defines a travel distance relative to a proximal starting position 306 of the firing shaft 150 where the control system monitors the torque of the firing motor 143. The control system 258 monitors the torque of the firing motor 143 as the firing shaft 150 travels along the detection zone 304 to determine whether the measured torque exceeds the bailout detection threshold 302. If the measured torque does not exceed the bailout detection threshold 302 within the detection zone 304, the control system can provide an alert that the surgical stapler 100 is in bailout mode. FIG. 6 includes an example bailout plot 308 illustrating an example measured torque within the detection zone 304 that does not exceed the bailout detection threshold 302 and thus results in the control system providing an alert that the surgical stapler is in bailout mode. Although the detection threshold 302 is shown as being approximately 4 inch-pounds and the detection zone 304 extends approximately 0.010 inch to approximately 0.100 inch, such values and ranges are provided as examples and other values and ranges are within the scope of this disclosure. As shown in FIG. 6, a buffer zone 310 can be included before the detection zone 304 where the control system ignores torque measurements to allow slack in the system and startup forces to not interfere with detection of the bailout mode.

If the bailout mechanism associated with the surgical stapler 100 has been activated, the firing motor 143 will essentially free-spin and experience very little torque (e.g., approximately 1 inch-pound). In contrast, if the bailout mechanism has not been activated, the control system 258 can detect a firing motor torque that is greater than the bailout detection threshold 302. As shown in FIG. 6, an example non-bailout line 312 illustrates approximate expected firing motor torque measurements as the firing shaft 150 is distally advanced. A spike 314 in measured torque indicates that the firing shaft 150 has engaged a lockout feature thereby locking out the surgical stapler and preventing advancement of the firing shaft 150. Once the firing shaft 150 is engaged with the lockout feature (e.g., located at a lockout point 316), the surgical stapler is placed in lockout and must be replaced from the surgical robot. As such, to ensure that the bailout test cycle does not cause lockout, the bailout test cycle does not distally advance the firing shaft 150 far enough to move the sled such that next time the firing shaft 150 is advanced, the firing shaft 150 would engage the lockout feature. Thus, the detection zone 304 does not extend to the lockout point 316, as shown in FIG. 6. The non-bailout line 312 also illustrates an expected measured increase in torque after the firing shaft 150 engages the jaws (e.g., jaw engagement point 318). However, as explained above, during performance of the bailout test cycle, the firing shaft 150 is not advanced past the detection zone 304 to ensure subsequent firing of the firing shaft 150 does not result in lockout.

Closure Tube Location Control

Articulation of the end effector can cause changes in the configuration and/or size of one or more aspects of the surgical stapler 100, such as changing the length of one or more drive assemblies and drive pathways. Such changes in the surgical stapler 100 due to articulation can affect the functioning of the surgical stapler compared to when the end effector 106 is not articulated. As such, the control system 258 can be configured to adjust one or more aspects of the surgical stapler 100 based on articulation of the end effector 106. For example, as described in greater detail below, the control system 258 can be configured to adjust one or more parameters or components of the closure assembly based on the articulation angle of the end effector 106 to protect against damage to the surgical stapler and ensure sufficient closing of the jaws.

FIGS. 7-8 illustrate a part of the closure assembly that controls opening and closing of the jaws 108, 110 of the end effector 106 (see FIGS. 1-2). As discussed above, the closure assembly includes a closure tube assembly 122 having a distal tube 126 pivotably coupled to a proximal tube 124 at a pivot joint 128. The pivot joint 128 is positioned along the length of the elongate shaft assembly 104 such that articulation of the end effector 106 causes the end effector 106 and the distal closure tube 126 to pivot relative to the proximal closure tube 124, as shown in FIG. 8. The resulting articulated configuration can be defined by an articulation angle θ, where the articulation angle θ is the angle between a central axis A8 of the proximal closure tube 126 and a central axis A8' of the distal closure tube 126. Additionally, the closure tube assembly 122 can be distally advanced along a stroke length that defines a length that the closure tube assembly 122 must travel in the distal direction to cause the jaws to move to the fully closed position. Proximally retracting the closure tube assembly 122 along the stroke length allows the jaws to move to the fully opened position.

As shown in FIG. 8, when the end effector 106 articulates and the distal tube 126 forms an articulation angle θ relative to the proximal closure tube 124, the closure tube assembly 122 becomes longer due to the added length created along the pivot joint 128. As the distal closure tube 126 pivots and the closure tube assembly 122 increases in length, the distal closure tube 126 distally advances (e.g., along the stroke length) thereby causing the jaws to close at least partway. Such preliminary closure of the jaws can limit or prevent proper tissue grasping and staple firing. Furthermore, since the distal closure tube 126 is caused to advance during articulation, the travel distance required by the closure tube assembly 122 to close the jaws decreases. As such, the stroke length effectively becomes shorter as a result of articulation of the end effector 106. If such shortening of the stroke length is not compensated for and the closure tube assembly 122 is caused to advance the entire stroke length, damage and possible malfunctioning of the surgical stapler can result. To overcome these issues, the control system 258 can be configured to modify, based on the articulation angle θ, a longitudinal position of the closure tube assembly 122 during articulation of the end effector 106 thereby maintaining the jaws in the open position, or to modify, based on the articulation angle θ, the stroke length of the closure tube assembly 122.

FIG. 9 illustrates a stroke length graph 400 showing how the control system 258 can modify the stroke length of the closure tube assembly 122 based on the articulation angle θ. Such modifying of the stroke length includes shortening the stroke length to a compensated stroke length (e.g., defined along the y-axis) as the articulation angle θ increases (e.g., defined along the x-axis). The compensated stroke length defines a length of travel of the closure tube assembly 122 in the distal direction to close the jaws, which is dependent upon the articulation angle θ and prevents over-travel of the closure tube assembly 122 causing damage to the surgical device.

For example, as shown in the stroke length graph 400, the stroke length of the closure tube assembly 122 to close the jaws is approximately 0.250 inches when the end effector 106 is not articulated, and the compensated stroke length is approximately 0.242 inches when the articulation angle θ is approximately 60 degrees. Such measurements are provided as examples only and can include any of a variety of angles and corresponding stroke lengths and compensated stroke lengths without departing from the scope of this disclosure. Furthermore, the relationship between the articulation angles θ and compensated stroke lengths is non-linear and the rate at which the compensated stroke length shortens increases as the articulation angle increases. For example, the decrease in compensated stroke lengths between 45 degrees and 60 degrees articulation is greater than the decrease in compensated stroke lengths between zero degrees and 15 degrees articulation. Although with this approach the control system is adjusting the stroke length based on the articulation angle θ to prevent damage to the surgical device (e.g., jamming the distal end of the closure tube assembly 122 in a distal position), the distal closure tube 126 is still allowed to advance during articulation, thereby potentially at least partly closing the jaws.

FIG. 10 illustrates a closure tube assembly positioning graph 500 showing one embodiment in which the control system 258 modifies a longitudinal position of the closure tube assembly 122 based on the articulation angle θ. Such modifying of the longitudinal position of the closure tube assembly 122 includes proximally retracting the closure tube assembly 122 by a compensation distance (e.g., defined along the y-axis) as the end effector 106 articulates and based on the articulation angle θ (e.g., defined along the x-axis). The compensation distance that the closure tube assembly 122 is proximally retracted prevents distal advancement of the distal closure tube 126 thereby maintaining the jaws in the open position during articulation. By proximally retracting the closure tube assembly 122 by the compensation distance during articulation, the closure tube assembly 122 can travel the stroke length starting form the proximally retracted position to close the jaws upon activation of the closure assembly.

For example, as shown in the closure tube assembly positioning graph 500, the compensation distance when the end effector is not articulated is zero and the compensation distance when the articulation angle θ is approximately 60 degrees is approximately 0.008 inches. In this example, the closure tube assembly 122 is retracted by a 0.008 inch compensation distance during articulation. As such, to close the jaws, the closure tube assembly can advance the stoke length starting from this retracted position. Such measurements are provided for example purposes only and can include any of a variety of angles and corresponding compensation distances without departing from the scope of the disclosure. As shown in FIG. 10, the relationship between the articulation angle θ and the compensation distance is non-linear and the rate at which the compensation distance lengthens increases as the articulation angle θ increases. For example, the increase in compensation distance between 45 degrees and 60 degrees is greater than the increase in compensation distance between zero degrees and 15 degrees.

Knife Location Control

Another actuation assembly affected by articulation of the end effector 106 includes the firing assembly. As shown in FIG. 3, the firing shaft 150 of the firing assembly includes an E-beam 154 coupled to a distal end of a flexible bar 152. The flexible bar 152 can include a plurality of ligation bands 164 that are flexible and extend along the articulation joint 120 of the elongate shaft assembly 104. As such, when the end effector 106 articulates and the articulation joint 120 bends, the flexible bar 152 bends along with the articulation joint 120. Bending of the flexible bar 152 causes the firing shaft 150 to increase in length, which can affect a number of activating steps performed by the firing assembly. For example, lengthening of the firing shaft 150 can affect the distance along which the firing shaft 150 travels until the E-beam 154 crosses a lockout point where the E-beam either enters a lockout thereby preventing advancement of the E-beam along the jaws 108, 110 or where the E-beam engages the sled thereby allowing advancement of the E-beam 154 along the jaws 108, 110. A cutting length that defines a distance the E-beam must travel to cut tissue grasped between the jaws is also affected by the change in length of the firing shaft 150 as a result of articulation of the end effector 106. Furthermore, a firing force defining the amount of force required to advance the E-beam 154 and cut tissue also increases at least as the angle of articulation along the articulation joint 120 increases. Other characteristics and aspects associated with firing of the firing assembly can be affected by articulation of the end effector, such as stretching of the end effector and speed of E-beam advancement, as will be discussed in greater detail below. The control system 258 can thus be configured to adjust and compensate for one or more of the above mentioned affected aspects of at least the firing assembly so that actuation of the firing assembly when the end effector is articulated does not result in damage to the surgical device or interfere with successful firing of the firing assembly (e.g., lockout detection, tissue cutting, etc.).

Knife Location Control—Low and High Power Zones

As discussed above, the surgical stapler includes a lockout mode when the E-beam 154 is caused to engage a lockout feature that can, for example, be associated with the lower jaw or cartridge. For example, the lockout mode is caused to occur if an unused cartridge is not properly loaded in the lower jaw thereby preventing unwanted advancement of the E-beam 154 along the jaws. If an unused cartridge is properly loaded in the lower jaw, a sled will be in a proximal starting position that allows the E-beam 154 to engage the sled, bypass the lockout feature, and advance along the jaws for cutting tissue captured between the jaws.

To ensure damage is not caused to the surgical device during lockout, such as damage to the E-beam 154 as it engages the lockout feature, the control system 258 can be configured to provide a lower power to the firing motor 143 until the E-beam advances past the lockout feature. By providing the lower power to the firing motor 143, a lower torque is provided by the firing motor 143 to the knife drive assembly 144 thereby advancing the E-beam 154 at a lower force. As such, at this lower power, if the E-beam were to engage the lockout feature, the E-beam would not be damaged or cause damage to the surgical device.

The control system 258 can also be configured to provide a higher power to the firing motor 143 after the E-beam advances past the lockout feature to ensure that the E-beam advances with sufficient force to cut tissue and that it will not stall out due to not having enough force to cut through the tissue. A lockout length can thus define a distally directed distance a firing bar driving the firing shaft 150 must travel to cause the E-beam 154 to bypass the lockout feature and thus when the lower power is provided to the firing motor 143. A cutting point can define an end to the lockout length where the higher power is provided to the firing motor 143 thereby advancing the E-beam 154 with sufficient force for cutting tissue. As will be discussed in greater detail below, the lockout length can change as a result of articulation of the end effector 106 due to the firing shaft 150 changing shape. More specifically, and as described above, the firing shaft 150 lengthens as the articulation angle (e.g., the articulation angle θ shown in FIG. 8) increases. As such, the control system can be configured to modify the lockout length based on the articulation angle of the end effector to ensure that the E-beam is advanced using appropriate power (e.g., low power along the modified lockout length and high power starting at the cutting point), and to ensure that the E-beam effectively cuts tissue and is protected against potential damage from engaging the lockout feature.

Figure 11:
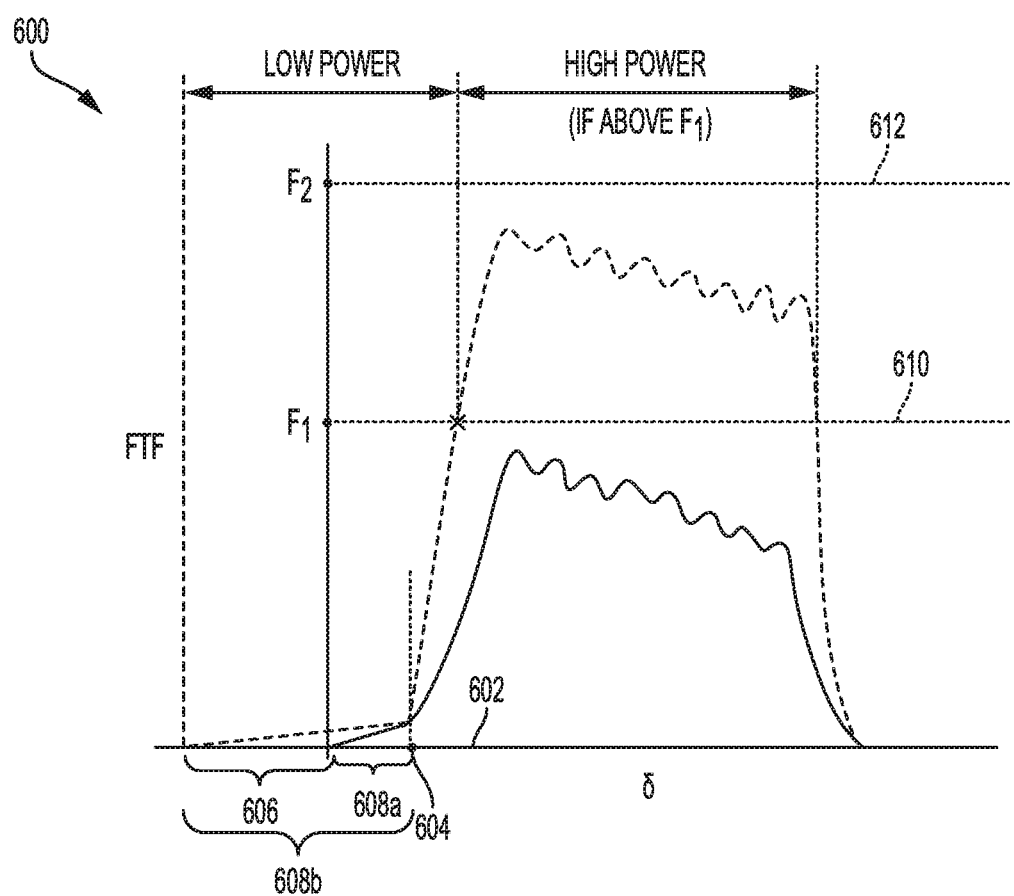
FIG. 11 is a lockout position graph with the x-axis defining firing rod and/or E-beam travel displacement and the y-axis defining the measured force or torque to advance the E-beam.

FIG. 11 illustrates a lockout position graph 600 showing the force to fire ("FTF") the E-beam as a function of firing bar travel displacement. The lockout position graph 600 identifies a cutting point 602 defining approximately a location where the E-beam is expected to start cutting tissue, which is positioned past a point of lockout 604. The point of lockout 604 defines a location along a firing length of travel where the E-beam would engage the lockout feature, such as if a new cartridge is not correctly positioned in the lower jaw thus placing the surgical stapler in lockout mode. The firing length of travel is defined as a travel distance extending between a proximal starting position of the E-beam (e.g., before actuation of the firing assembly) to when the E-beam is adjacent a distal end of the jaws. As discussed above, the control system delivers a low power to the firing motor 143 to advance the E-beam at a low force up to the cutting point 602 and a high power is provided to the firing motor 143 to advance the E-beam at a high force beginning at the cutting point 602.

The location of the point of lockout 604 and cutting point 602 can change relative to the proximal starting position of the E-beam based on the articulation angle resulting from articulation of the end effector. For example, as the articulation angle increases, the firing shaft 150 can increase in length thereby advancing the E-beam 154 distally towards the point of lockout 604 and cutting point 602. To compensate for such lengthening, the control system 258 can retract the firing shaft 150 a compensation distance 606 (as shown in FIG. 11) equal to the length added to the firing shaft 150 as a result of articulation. The firing shaft 150 can be retracted as the end effector articulates or after articulation is complete, but before firing of the firing assembly.

As a result of the retracted firing shaft 150, as shown in FIG. 11, the control system 258 determines a compensated lockout length 608b defining a distance the firing bar travels to advance the E-beam to the cutting point 602 before switching from low to high power. As shown in FIG. 11, the compensated lockout length 608b is greater than a lockout length 608a when the end effector is not articulated. Furthermore, the greater the articulation angle, the greater the compensated lockout length.

Alternatively, rather than the control system 258 moving the position of the firing rod and E-beam based on the articulation angle, the control system 258 can shorten the lockout length 608a by an amount of length that the firing shaft 150 increased as a result of the articulation angle. As such, the compensated lockout length 608b would shorten as the articulation angle increased.

The control system can also monitor the firing motor toque to protect against damage to the firing motor 143 and/or surgical device, such as preventing to attempt further travel of the E-beam if the E-beam engages the lockout feature or if an object is preventing the E-beam from advancing. As shown in FIG. 11, the control system can include a predefined low power force threshold 610 that is applied along the firing length of travel up to the cutting point 602 and a predefined high power force threshold 612 that is applied along the firing length of travel after the cutting point 602. For example, the low power force threshold 610 can be less than the high power force threshold 612 because prior to cutting tissue (e.g., before the cutting point 602), the forces required to advance the E-beam should be much lower compared to forces required to advance the E-beam to cut tissue (e.g., after the cutting point 602). Furthermore, since the force to advance the E-beam in both the low and high power modes will increase as the end effector articulates, the control system can increase the low and high power force thresholds 610, 612 to account for such expected increases in force, thereby preventing unnecessary triggering of a system error or interfering with firing of the firing assembly. For example, if the measured force to advance the E-beam exceeds either the low or high power force thresholds 610, 612, the control system 258 can provide an alert and/or prevent the E-beam from advancing along the firing length of travel. As such, the control system can effectively provide sufficient forces to the E-beam to protect the E-beam from lockout mode related damages and provide the E-beam with sufficient force to cut tissue. In addition, the control system 258 can also monitor forces to advance the E-beam to ensure the firing motor 143 is not overloaded and/or detect if the E-beam is in lockout mode thereby preventing damage to the surgical stapler.

Knife Location Control—Stroke Length

As discussed above, the firing shaft 150 lengthens as the articulation angle increases, which can cause the E-beam 154 to advance along the firing length of travel towards the jaws before the firing assembly is activated. In addition, other aspects of the surgical stapler and firing of the firing assembly are affected as a result of articulation of the end effector. For example, as the articulation angle (e.g., the articulation angle θ shown in FIG. 8) increases, a force supplied by the firing motor 143 to advance the firing rod and firing shaft 150 increases. Such increase in force is required to compensate for the additional force required to advance the firing shaft 150 along the articulated articulation joint. Additionally, the force required to advance the firing shaft 150 can further increase as some tissue properties (e.g., thickness and/or density) increase. Such increased forces applied to at least the firing bar and firing shaft 150 as the articulation angle and/or tissue properties increase results in lengthening of the overall firing length of travel.

For example, such lengthening of the firing length of travel can be a result of one or more materials or components of the surgical stapler 100 stretching when placed under high loads. For example, the cartridge and/or elongate shaft can be caused to stretch in length as the E-beam 154 is forced along the jaws at a high load, such as when the end effector 106 is articulated and/or thick tissue is being cut by the E-beam 154. As such, the control system 258 can be configured to modify, based on at least the articulation angle, the force provided by the firing motor 143 to ensure the E-beam 154 advances with sufficient force to effectively cut tissue grasped between the jaws regardless of the articulation angle. The control system 258 can also control the speed at which the E-beam 154 advances, such as to reduce stretching of the surgical stapler 100 and/or reduce the amount of needed force to cut tissue.

Figure 12:
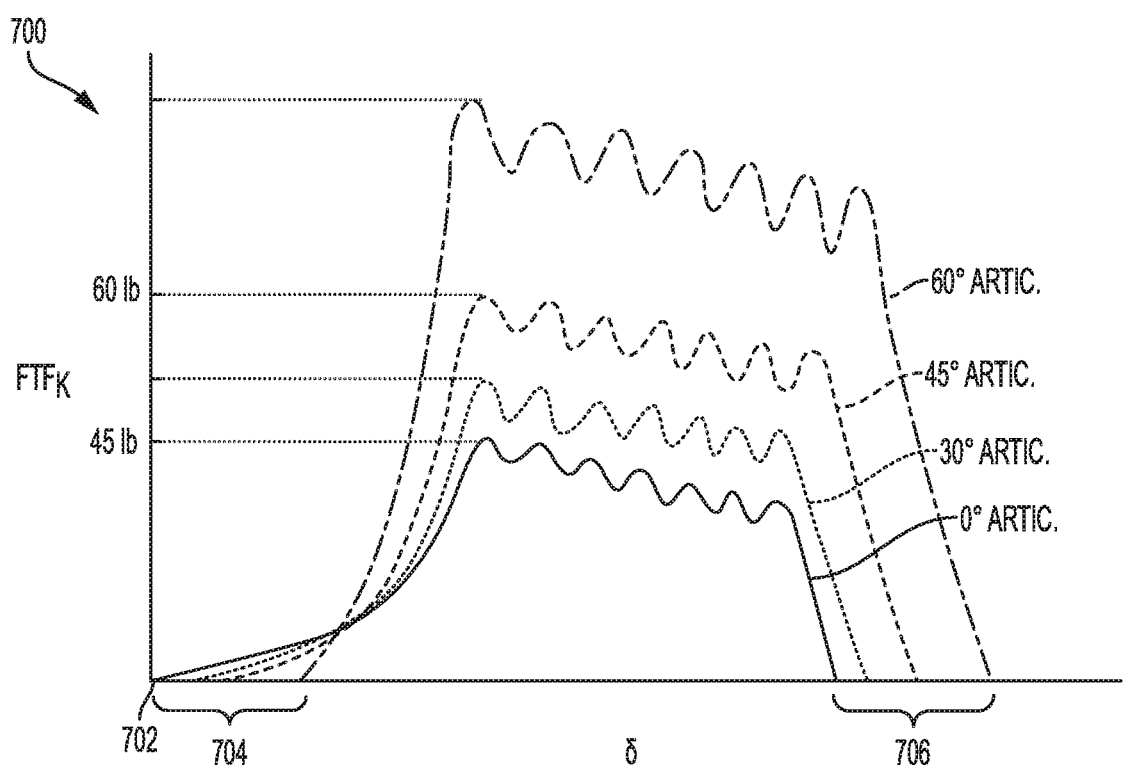
FIG. 12 is a firing graph with the x-axis defining distance of travel of a knife or E-beam along the firing length of travel, and the y-axis defining expected firing forces.

FIG. 12 illustrates a firing graph 700 showing the expected firing forces, which are defined herein as forces provided by the firing motor 154 to advance the E-beam 154 along the firing length of travel, as a function of distance of travel of the knife or E-beam 154 along the firing length of travel. The firing graph 700 illustrates expected firing forces as the E-beam 154 travels along the firing length of travel at various exemplary articulation angles (e.g., 0 degrees, 30 degrees, 45 degrees, and 60 degrees) of the end effector. Although some articulation angles and associated expected firing forces are provided in the firing graph 700, other articulation angles and firing forces are within the scope of this disclosure.

As shown in FIG. 12, a straight shaft having a zero degree articulation angle will have lower expected firing forces compared to an articulated shaft. Additionally, at zero degree articulation the firing shaft 150 is not lengthened so the E-beam will begin traveling along the firing length of travel starting from a proximal starting position 702. In comparison, as the articulation angle increases, the E-beam 154 increasingly advances distally along the firing length of travel prior to actuation of the firing assembly, such as within a firing shaft offset range 704, as shown in FIG. 12. Additionally, as the articulation angle increases, the expected firing forces increase.

Furthermore, although at zero degree articulation there is no positional offset of the E-beam from the proximal start position 702 and an expected force to fire is relatively the lowest, the E-beam 154 can experience greater loads, such as having to cut through thick tissue, thereby stretching the surgical stapler and elongating the firing length of travel. Similarly and even to a greater extent, as the articulation angle increases and greater loads are required to overcome loss in forces associated with advancing the firing shaft 150 around the bent articulation joint, stretch of the firing length of travel increases. Such increase in the firing length of travel can be even further increased if the E-beam encounters, for example, thick tissue between the jaws. For example, as shown in FIG. 12, the firing length of travel can be increased within a stretch offset range 706 at least as the articulation angle increases.

The control system 258 described herein can be configured to utilize the expected firing forces based on articulation angles to adjust force thresholds in the surgical stapling system. For example, when the end effector is not articulated, the control system can treat sensed motor torque forces above 45 pounds (e.g., the maximum expected firing force at zero degree articulation) as an indication of an error (e.g., cutting obstruction, lockout, etc.). Similarly, for example, when the articulation angle is at 45 degrees, the control system can treat sensed motor torque forces above 60 pounds (e.g., the maximum expected firing force at 45 degree articulation angle) as an indication of an error. Once the error is detected by the control system, the control system can adjust the speed of E-beam advancement, including stopping advancement, to thereby reduce torsional loads and prevent damage to the firing motor 143 and/or E-beam 154.

The control system 258 can also be configured to ensure the E-beam 154 effectively cuts tissue and travels the firing length of travel, including the elongated firing length of travel due to stretch in the system, while also compensating for any added length in the firing shaft 150 due to articulation of the end effector. As such, the control system can shorten the firing length of travel by the added firing shaft 150 length due to articulation (e.g., shown in the firing shaft offset range 704 in FIG. 12) and also lengthen the firing length of travel the distance the system is expected to stretch (e.g., shown in the stretch offset range 706 in FIG. 12) based on the articulation angle and torsional loads sensed on the firing motor (e.g., caused by tissue thickness). By adjusting the firing length of travel, the control system ensures that the knife of the E-beam effectively cuts the tissue captured between the jaws and also ensures that the E-beam or jaws do not get damaged by the E-beam over-traveling and jamming into a distal end of the jaws.

Knife Location Control—Force Thresholds

In some embodiments, the control system 258 can include a plurality of predefined force thresholds that assist the control system in determining a position of the E-beam and/or articulation angle of the shaft and appropriately controlling at least one motor based on such determination. For example, the force thresholds can change depending on a length of travel of the firing bar configured to translate the firing shaft 150, and such force thresholds can be compared to a measured torsional force of the one or more motors in communication with the control system. Comparison of the measured torsional forces against the force thresholds can provide a dependable way for the control system 258 to determine a location of the E-beam 154 and/or articulation of the end effector 106. This can allow the control system 258 to appropriately control the one or more motors (e.g., reduce or stop torsional loads) to ensure proper firing of the firing assembly and articulation of the end effector, as well as prevent against damage to the system, as will be described in greater detail below.

Figure 13:
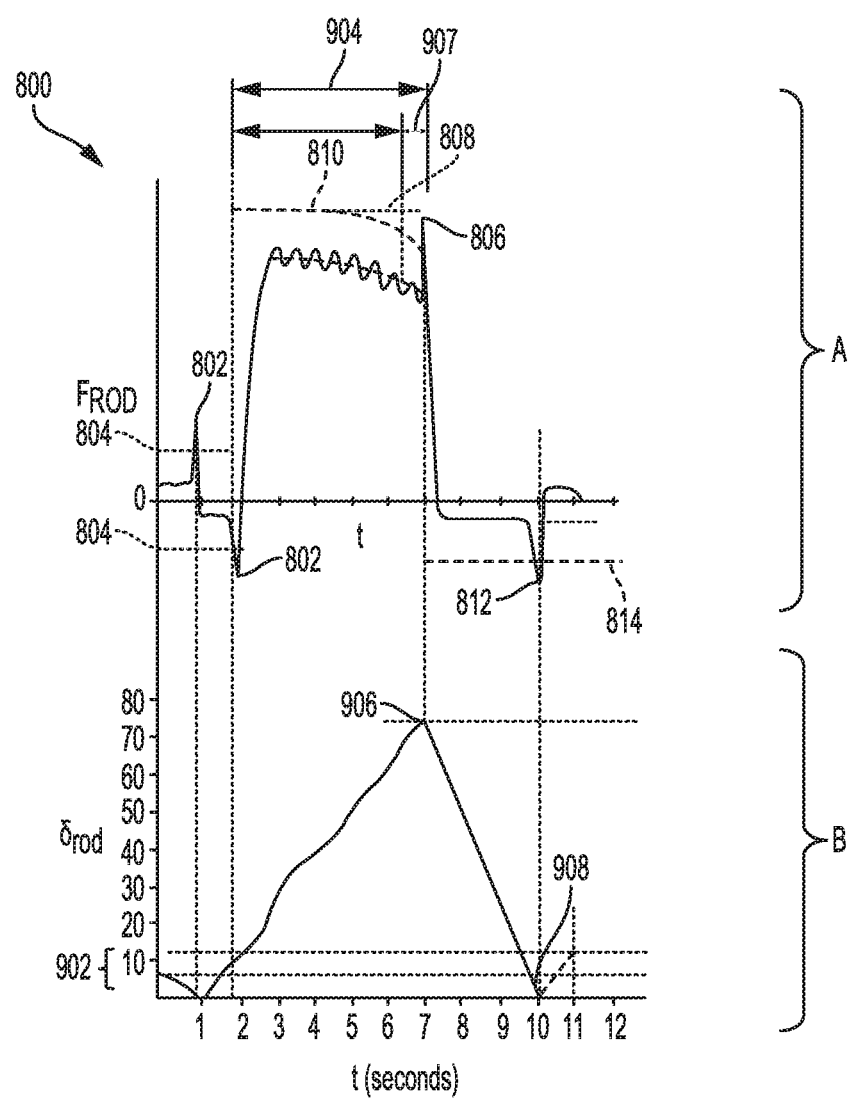
FIG. 13 is a force graph shown in section A and a related displacement graph shown in section B, where the force graph and the displacement graph have an x-axis defining time, a y-axis of the displacement graph defines a travel displacement of a firing rod, and a y-axis of the force graph defines a sensed torsional force on a motor that is configured to advance the firing rod.

FIG. 13 illustrates a force and displacement graph 800 including measured forces in section A that are related to measured displacements in section B. Both section A and B have an x-axis defining time (e.g., seconds). The y-axis of section B defines a travel displacement (e.g., in millimeters) of a firing rod and the y-axis of section A defines a force applied to the firing bar to thereby advance the firing shaft 150. As shown in section A, travel of the firing bar within a first articulation range 902 (e.g., a first approximately 12 mm of travel) causes the end effector 106 to articulate. For example, at the 12 mm displacement position the end effector 160 is fully articulated to the right and is mechanically unable to articulate further. As a result of being at full articulation the torsional force on the motor will increase and the control system can sense an articulation force peak 802 that exceeds a predefined articulation threshold 804, as shown in section A. The control system 258 can include more than one predefined articulation threshold 804 for sensing more than one max articulation direction (e.g., left articulation and right articulation). After the control system detects an articulation force peak 802 that exceeds the predetermined articulation threshold 804, the control system can reduce or stop actuation of the motor thereby protecting at least the motor from damage.

After the firing bar advances past the articulation range 902, a shifting mechanism within the surgical stapler 100 can cause further distal travel of the firing bar to cause distal travel of the firing shaft 150. For example, as shown in section B, travel between approximately 12 mm and 70 mm of travel displacement can cause the E-beam 154 to advance along a firing stroke 904 and cut tissue captured between the jaws, however, other lengths of travel are within the scope of this disclosure. In this example, a maximum firing stroke position 906 of the E-beam occurs at 70 mm travel. At this point, the E-beam or knife abuts a distal end of the cartridge or jaw thereby increasing torsional forces on the motor and causing a knife travel force peak 806, as shown in section A, to be sensed by the control system 258. As shown in section A, the control system 258 can include a motor threshold 808 and an end of knife travel threshold 810 that branches off from the motor threshold 808 and decreases (e.g., non-linearly) as the E-beam approaches the maximum firing stroke position 906.

The control system can be configured to monitor the sensed motor torsional force during at least the last part of distal travel 907 (e.g., last 10 percent of the firing stroke 904) of the E-beam before reaching the maximum firing stroke position 906. While monitoring along such last part of distal travel 907, the control system can cause the motor to reduce torsional forces to thereby reduce the load on the E-beam. This can protect damage to the surgical stapler, including the E-beam, by reducing loads on the E-beam as the E-beam approaches the maximum firing stroke position 906 thereby reducing impact of the E-beam against the distal end of the cartridge or jaw. As mentioned above, such impact can cause a knife travel force peak 806, which can exceed the knife travel threshold 810 but not the motor threshold 808 thereby not damaging the motor. As such, the control system 258 can stop actuation of the motor after the knife travel force peak 806 exceeds the knife travel threshold 810 and before the knife travel force peak 806 exceeds the motor threshold 808 thereby protecting the motor from damage. Furthermore, the increasing reduction in the knife travel threshold 810 prevents the control system from preliminarily thinking that the E-beam has reached the maximum firing stroke position 906.

After the control system 258 has detected a knife travel force peak 806 exceeding the knife travel threshold 810, the control system can confirm a position of the E-beam (e.g., at 70 mm displacement and/or at end of firing stroke 904) and can retract the firing bar based on such known displacement position to reset the E-beam in a most proximal position 908 (e.g., 0 mm displacement). At the most proximal position 908, a knife retraction force peak 812 that exceeds a predefined knife retraction threshold 814, as shown in section A, can be sensed by the control system 258. At this point, the control system can recalibrate, if needed, and associate the position of the E-beam as being in a home position where subsequent advancement of the firing rod in the distal direction (e.g., approximately 12 mm in length) will cause the shifter to disengage the E-beam from the firing bar. Once disengaged, firing bar travel within the articulation range 902 will again cause articulation of the end effector 106.

As such, the control system 258 can sense torsional forces on the motor controlling travel of the firing bar and compare such sensed torsional forces against a plurality of thresholds to determine a position of the E-beam or angle of articulation of the end effector and thereby appropriately control the motor to prevent damage to the motor, as well as confirm positioning of the firing bar and/or E-beam.

Knife Location Control—Controlled Lockout

In certain embodiments, it can be important for the control system 258 to know exactly where the E-beam home position is so the control system can either position the E-beam 154 in the home position or know an exact offset distance the E-beam is from the home position prior to firing the firing assembly. For example, the home position can be a starting position where all other subsequent firing steps are referenced from. As such, if the control system 258 fires the firing assembly with an incorrect understanding of where the E-beam is located relative to the home position, a number of errors can result, including undercutting the tissue or damaging the surgical device due to jamming the E-beam into the end of the jaws (e.g., attempting to overshoot the firing length of travel). Furthermore, correctly finding the home position can be particularly difficult after the E-beam has been fired, such as due to changes in one or more properties of the surgical stapler during a previous firing of the E-beam (e.g., stretching and/or bending of one or more components of the surgical stapler). As such, in some embodiments, the control system 258 is configured to run a home detection cycle for determining the home position to thereafter position the E-beam correctly in the home position and/or calibrate the position of the E-beam based on a measured offset of the E-beam from the home position.

Figure 14A:
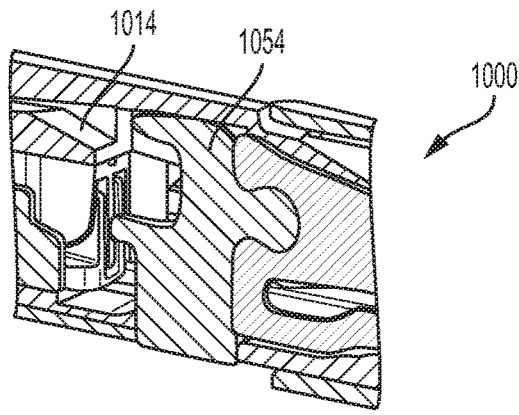
FIG. 14A is a cut-away side perspective view of a portion of a firing shaft shown when the jaws of an end effector are in the closed position and the control system of FIG. 4 is running a home detection cycle.
Figure 14B:
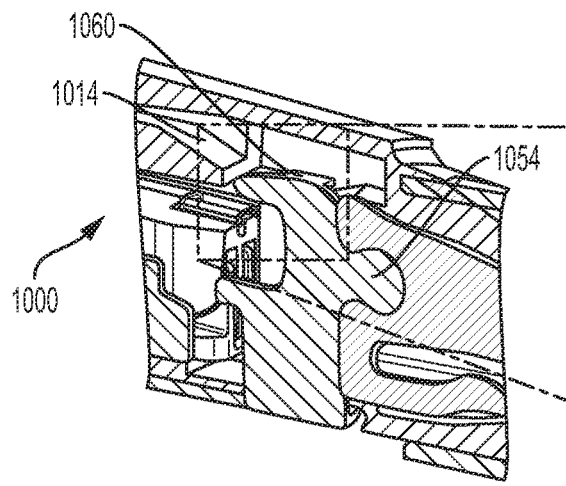
FIG. 14B is a cut-away side perspective view of a portion of the firing shaft of FIG. 14A shown when the jaws of the end effector are in a partially open position and the control system of FIG. 4 is running the home detection cycle.
Figure 14D:
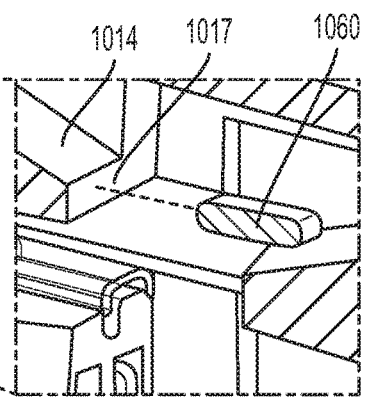
FIG. 14D is an enlarged view of a lateral guide of the firing shaft of FIG. 14B.
Figure 14C:
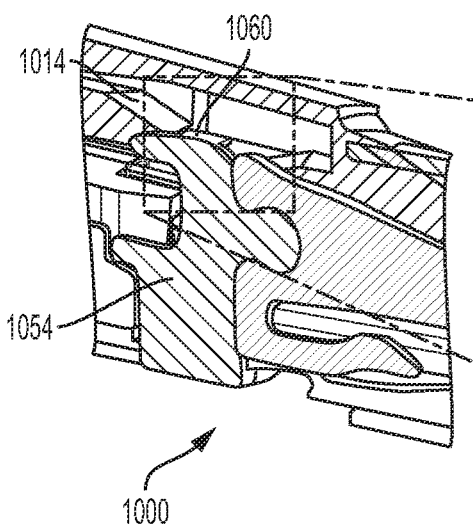
FIG. 14C a cut-away side perspective view of a portion of the firing shaft of FIG. 14B shown when the firing shaft has been moved distally and the control system of FIG. 4 is running the home detection cycle.
Figure 14E:
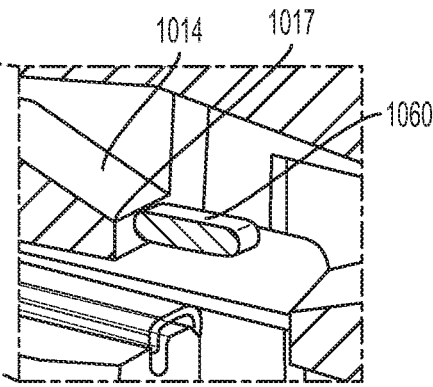
FIG. 14E is an enlarged view of a lateral guide of the firing shaft of FIG. 14C shown when the firing shaft has moved distally.

FIGS. 14A-14E illustrate exemplary steps that can be performed by the control system 258 while running a home detection cycle. In FIGS. 14A-14E, the steps are performed using a surgical stapler 1000 that can generally be similar to surgical stapler 100 shown in FIG. 1. As shown in FIG. 14A, an E-beam 1054 can be in a proximal position relative to an anvil 1014, such as after being proximally retracted subsequent to firing of the E-beam 1054. For example, the jaws can still be in a closed position, as shown in FIG. 14A. As shown in FIGS. 14B and 14D, as part of the home detection cycle, the control system can at least partially open the jaws thereby aligning a proximal end 1017 of the anvil 1014 with an upper lateral guide 1060 of the E-beam 1054 (e.g., such as the upper lateral guide feature 160 shown in FIG. 3). Once at the proximal end of the anvil 1014 and the upper lateral guide 1060 are aligned, the control system can advance the E-beam 1054 towards the anvil 1014 until the upper lateral guide 1060 runs into the proximal end 1017 of the anvil 1014, as shown in FIGS. 14C and 14E. When the upper lateral guide 1060 runs into the proximal end 1017 of the anvil 1014, the control system can detect a spike in torsional force in a motor controlling the advancement of the E-beam (e.g., the knife motor 143), such as detect a spike in force that exceeds a predefined force threshold associated with the home detection cycle.

Once such spike in force is detected, the control system 258 can stop actuation of the motor and calibrate the position of the E-beam 1054 relative to a fixed point (e.g., the proximal end 1017 of the anvil 1014). For example, the control system can proximally retract the E-beam 1054 a predefined distance to the home position relative to this fixed point. Once the control system has positioned the E-beam 1054 in the home position, the control system can effectively fire the E-beam 1054 from an exact, known position, e.g., the home position, thereby preventing, for example, undercutting the tissue or damaging the surgical stapler due to attempting to overshoot the firing length of travel.

Computer Systems

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 15:
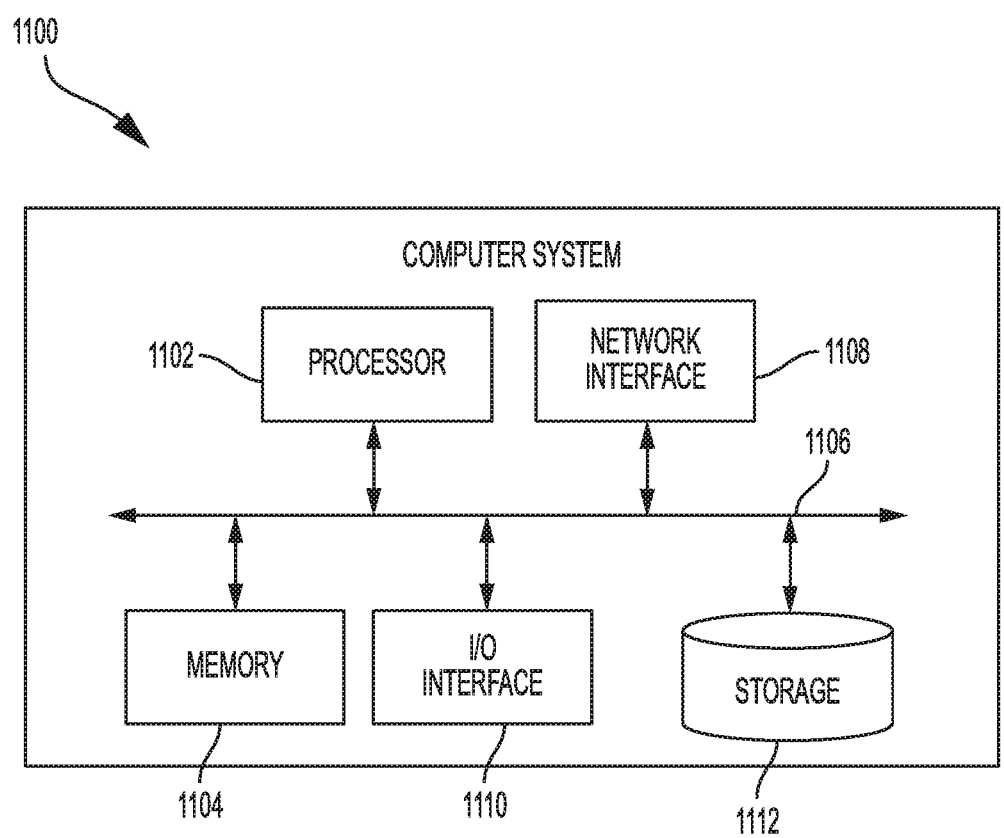
FIG. 15 is one exemplary embodiment of a computer system.

FIG. 15 illustrates one exemplary embodiment of a computer system 1100. As shown, the computer system 1100 includes one or more processors 1102 which can control the operation of the computer system 1100. "Processors" are also referred to herein as "controllers." The processor(s) 1102 can include any type of microprocessor or central processing unit (CPU), including programmable general-purpose or special-purpose microprocessors and/or any one of a variety of proprietary or commercially available single or multi-processor systems. The computer system 1100 can also include one or more memories 1104, which can provide temporary storage for code to be executed by the processor(s) 1102 or for data acquired from one or more users, storage devices, and/or databases. The memory 1104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1100 can be include a bus system 1106. The illustrated bus system 1106 can include an abstraction that represents any one or more separate physical busses, communication lines/interfaces, and/or multi-drop or point-to-point connections, connected by appropriate bridges, adapters, and/or controllers. The computer system 1100 can also include one or more network interface(s) 1108 that enable the computer system 1100 to communicate with remote devices, e.g., motor(s) coupled to the drive system that is located within the surgical device or a robotic surgical system, one or more input/output (IO) interface(s) 1110 that can include one or more interface components to connect the computer system 1100 with other electronic equipment, such as the sensors located on the motor(s), and one or more storage device(s) 1112. The storage device(s) 1112 can include any conventional medium for storing data in a non-volatile and/or non-transient manner. The storage device(s) 1112 can thus hold data and/or instructions in a persistent state, i.e., the value(s) are retained despite interruption of power to the computer system 1100.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapling system, comprising:
a stapling tool having a housing and an instrument shaft extending therefrom with an end effector at a distal end thereof, the end effector including a first jaw having a staple cartridge with a plurality of staples therein, and a second jaw in the form of an anvil, the first and second jaws being movable between an open position and a closed position, and the end effector being articulatable relative to the instrument shaft, the stapling tool including
a clamping assembly having a cam mechanism configured to translate distally to cam the anvil into a fully closed position, the stapling tool including
an articulation assembly configured to articulate the end effector to a plurality of angular orientations relative to the instrument shaft, and the stapling tool including
a firing assembly configured to progressively drive the plurality of staples through the staple cartridge toward the anvil for stapling tissue engaged between the staple cartridge and the anvil; and
an electronic control system configured to communicate with the stapling tool and to control movement of the articulation assembly, the clamping assembly, and the firing assembly, the electronic control system being configured to adjust, during articulation of the end effector, a longitudinal position of the cam mechanism based on an angular orientation of the end effector to thereby maintain the anvil in the fully open position.

2. The surgical stapling system of claim 1, wherein a change in the longitudinal position of the cam mechanism has a non-linear relationship with the angular orientation of the end effector.

3. The surgical stapling system of claim 1, wherein the control system is configured to cause the cam mechanism to proximally retract as the angular orientation of the end effector increases.

4. The surgical stapling system of claim 1, wherein the control system is configured to proximally retract the cam mechanism at an increasing rate as the angular orientation of the end effector increases.

5. The surgical stapling system of claim 1, wherein the cam mechanism includes a distal closure tube pivotably coupled to a proximal closure tube, and wherein the distal closure tube is coupled to the anvil such that distal advancement of the cam mechanism causes the distal closure tube to apply a closing force to the anvil thereby positioning the anvil in the closed position.

6. The surgical system of claim 1, wherein the housing comprises a tool mounting portion configured to mount to a motor housing on a surgical robot.

7. A surgical stapling system, comprising:
an electromechanical tool having
an elongate shaft having an end effector at a distal end thereof, the end effector being configured to articulate relative to the elongate shaft such that the end effector can be positioned in a plurality of angular orientations, and the end effector a first jaw having a staple cartridge with a plurality of staples disposed therein, and a second jaw comprising an anvil, the first and second jaws being movable between open and closed positions,
a plurality of drive assemblies including
a clamping assembly having a cam mechanism configured to translate proximally to cam the anvil into a fully open position, an articulation assembly configured to articulate the end effector to an angular orientation relative to the instrument shaft, and a firing assembly configured to progressively drive the plurality of staples through the staple cartridge toward the anvil for stapling tissue engaged between the staple cartridge and the anvil; and an electronic control system configured to communicate with the electromechanical tool and to control the plurality of drive assemblies, the electronic control system being configured to modify, based on an angular orientation of the end effector and during articulation of the end effector, a longitudinal position of the cam mechanism to thereby maintain the anvil in the fully open position or modify, based on an angular orientation of the end effector, a stroke length of the clamping assembly to cause the first and second jaws to move into the closed position.

8. The surgical system of claim 7, wherein a relationship between a change in the stroke length and a change in the angular orientation of the end effector is non-linear.

9. The surgical system of claim 7, wherein the control system is configured to decrease the stroke length as the angular orientation of the end effector increases.

10. The surgical system of claim 7, wherein the control system is configured to decrease the stroke length at an increasing rate as the angular orientation of the end effector increases.

11. The surgical system of claim 7, wherein a change in the longitudinal position of the cam mechanism has a non-linear relationship with the angular orientation of the end effector.

12. The surgical system of claim 7, wherein the control system is configured to cause the cam mechanism to proximally retract as the angular orientation of the end effector increases.

13. The surgical system of claim 7, wherein the control system is configured to proximally retract the cam mechanism at an increasing rate as the angular orientation of the end effector increases.

14. The surgical system of claim 7, wherein the cam mechanism includes a distal closure tube pivotably coupled to a proximal closure tube, and wherein the distal closure tube is coupled to the anvil such that distal advancement of the cam mechanism causes the distal closure tube to apply a closing force to the anvil thereby positioning the anvil in the closed position.

15. The surgical system of claim 7, further comprising a housing with the elongate shaft extending therefrom, wherein the housing comprises a tool mounting portion configured to mount to a motor housing on a surgical robot.

* * * * *